(12) United States Patent
Jacob

(10) Patent No.: US 6,225,325 B1
(45) Date of Patent: May 1, 2001

(54) USE OF ALKYLATED IMINOSUGARS TO TREAT MULTIDRUG RESISTANCE

(75) Inventor: Gary S. Jacob, Creve Coeur, MI (US)

(73) Assignee: G.D. Searle & Company, Chicago, IL (US)

( * ) Notice: Subject to any disclaimer, the term of this patent is extended or adjusted under 35 U.S.C. 154(b) by 0 days.

(21) Appl. No.: 09/189,177

(22) Filed: Nov. 10, 1998

Related U.S. Application Data

(60) Provisional application No. 60/065,051, filed on Nov. 10, 1997.

(51) Int. Cl.⁷ .......................... A01N 43/40; A61K 31/445
(52) U.S. Cl. ................................................. 514/328
(58) Field of Search ............................................. 514/328

(56) References Cited

U.S. PATENT DOCUMENTS

| | | | |
|---|---|---|---|
| 452,406 | 6/1985 | Mughal | 424/19 |
| 3,590,028 | 6/1971 | Arcamone | 260/210 |
| 4,012,448 | 3/1977 | Smith et al. | 260/591 |
| 4,065,562 | 12/1977 | Ohata et al. | 424/267 |
| 4,182,767 | 1/1980 | Murai et al. | 424/267 |
| 4,260,622 | 4/1981 | Junge et al. | 424/267 |
| 4,327,725 | 5/1982 | Cortese et al. | 128/260 |
| 4,533,668 | 8/1985 | Matsumura et al. | 514/321 |
| 4,611,058 | 9/1986 | Koebernick | 546/242 |
| 4,612,008 | 9/1986 | Wong et al. | 604/892 |
| 4,639,436 | 1/1987 | Junge et al. | 514/24 |
| 4,765,989 | 8/1988 | Wong et al. | 424/473 |
| 4,783,337 | 11/1988 | Wong et al. | 424/468 |
| 4,806,650 | 2/1989 | Schröder et al. | 546/242 |
| 4,849,430 | 7/1989 | Fleet et al. | 514/315 |
| 4,880,830 | 11/1989 | Rhodes | 424/470 |
| 4,957,926 | 9/1990 | Jacob et al. | 514/315 |
| 5,003,072 | 3/1991 | Partis et al. | 546/243 |
| 5,011,829 | 4/1991 | Hirsch et al. | 514/50 |
| 5,030,638 | 7/1991 | Partis et al. | 514/315 |
| 5,041,441 | 8/1991 | Radin et al. | 514/237.8 |
| 5,068,112 | 11/1991 | Samejima et al. | 424/495 |
| 5,144,037 | 9/1992 | Partis et al. | 546/116 |
| 5,151,519 | 9/1992 | Behling et al. | 546/219 |
| 5,190,765 | 3/1993 | Jao et al. | 424/473 |
| 5,264,356 | 11/1993 | Rohrschneider | 435/236 |
| 5,281,724 | 1/1994 | Behling | 549/334 |
| 5,310,745 | 5/1994 | Partis | 514/315 |
| 5,331,096 | 7/1994 | Koszyk et al. | 546/115 |
| 5,411,970 | 5/1995 | Partis et al. | 514/315 |
| 5,451,679 | 9/1995 | Barta et al. | 546/219 |
| 5,472,969 | 12/1995 | Platt et al. | 514/315 |
| 5,491,135 | 2/1996 | Blough | 514/115 |
| 5,525,616 | 6/1996 | Platt et al. | 514/315 |
| 5,536,732 | 7/1996 | Lesur et al. | 514/317 |
| 5,595,981 | 1/1997 | Barta et al. | 514/63 |
| 5,612,480 | 3/1997 | Barta et al. | 544/180 |
| 5,663,342 | 9/1997 | Barta et al. | 546/6 |

FOREIGN PATENT DOCUMENTS

| | | | |
|---|---|---|---|
| 0 324 328 | 7/1989 | (EP) | A61K/31/445 |
| 0 350 012 | 1/1990 | (EP) | A61K/31/445 |
| 0 367 748 | 5/1990 | (EP) | C07D/211/46 |
| 0 401 194 A1 | 5/1990 | (EP) | . |
| 0 449 026 | 10/1991 | (EP) | C07D/491/04 |
| 0 494 850 | 7/1992 | (EP) | C07D/211/46 |
| 0 566 556 | 10/1993 | (EP) | C07D/211/40 |
| 0 477 160 B1 | 4/1996 | (EP) | . |
| 2020278 | 3/1979 | (GB) | C07D/211/40 |
| WO87/03903 | 7/1987 | (WO) | C12N/05/00 |
| WO 94/04546 | 4/1993 | (WO) | . |
| WO93/18763 | 9/1993 | (WO) | A61K/31/195 |
| WO95/06061 | 3/1995 | (WO) | C07K/5/03 |
| WO95/19172 | 7/1995 | (WO) | A61K/31/445 |
| WO95/22975 | 8/1995 | (WO) | A61K/31/445 |
| WO96/40110 | 12/1996 | (WO) | A61K/31/35 |
| WO97/00881 | 1/1997 | (WO) | C07H/17/02 |
| WO98/35685 | 8/1998 | (WO) | A61K/31/70 |

OTHER PUBLICATIONS

Dalton, et al., "A Phase II Randomized Study of Oral Verapamil as a Chemosensitizer to Reverse Drug Resistance in Patients with Refractory Myeloma," Feb. 1, 1995, Cancer, vol. 75, No. 3, pp. 815–820.

Jacob et al., "Aminosugar Attenuation of HIV Infection," 1992, Natural Products as Antiviral Agents, pp. 137–152.

Karpas, et al., "Aminosugar Derivatives as Potential Anti–Human Immunodeficiency Virus Agents," Dec., 1988, Proc. Natl. Acad. Sci., vol. 85, pp. 9229–9233.

Welsh, et al., "Accumulation of Fatty Alcohol in MCF–7 Breast Cancer Cells," Nov. 15, 1994, Archives of Biochemistry and Biophysics, vol. 315, No. 1, pp. 41–47.

Blum et al., "Antiviral Therapy of Hepatitis B Virus Infection: Blocking Viral Gene Expression," Jun. 1995, Elsevier Science, B.V., Advanced Drug Delivery Reviews 17, pp. 321–331.

Lu, et al., "Aberrant Trafficking of Hepatitis B Virus Glycoproteins in Cells in Which N–glycan Processing is Inhibited," Mar. 1997, Proc. Natl. Acad. Sci., vol. 94, pp. 2380–2385.

Korba, et al., "Antiviral Effectiveness of 3TC, Famciclovir, and Interferon Against Chronic WHV Replication–Potential for Combination Therapy," Sep. 1996, Molecular Biology of Hepatitis B Viruses Meeting, p. 201.

(List continued on next page.)

Primary Examiner—Dwayne C. Jones
(74) Attorney, Agent, or Firm—Senniger, Powers, Leavitt & Roedel

(57) ABSTRACT

Methods and compositions for preventing, reducing, or reversing multidrug resistance (MDR) during cancer chemotherapy in patients undergoing treatment with therapeutically effective amounts of chemotherapeutic agents are provided. The methods comprise administering an anti-MDR effective amount of an N-substituted-1,5-dideoxy-1,5-imino-D-glucitol or galactitol iminosugar to a patient.

42 Claims, No Drawings

OTHER PUBLICATIONS

Dienstag, et al., "A Preliminary Trial of Lamivudine for Chronic Hepatitis B Infection," Dec. 21, 1995, The New England Journal of Medicine, vol. 333, No. 25, pp. 1657–1661.

Holleran, et al., "Characterization of Cellular Lipids in Doxorubicin–Sensitive and –Resistant P388 Mouse Leukemia Cells," 1986, Cancer Chemother Pharmacol, 17:11–15.

Fisher, et al., "Clinical Studies with Modulators of Multidrug Resistance," Apr. 1995, Drug Resistance in Clinical Oncology and Hematology, vol. 9, No. 2, pp. 363–382.

Raderer, et al., "Clinical Trials of Agents that Reverse Multidrug Resistance," Dec. 15, 1993, Cancer, vol. 72, No. 12, pp. 3553–3563.

Tan, et al., "Chemical Modification of the Glucosidase Inhibitor 1–Deoxynojirimycin," Aug. 15, 1991, The Journal of Biological Chemistry, Vo. 266, No. 22, pp. 14504–14510.

Wang, et al., "Chemo–enzymatic Synthesis of Five–membered Azasugars as Inhibitors of Fucosidase and Fucosyltransferase: An Issue Regarding The Stereochemistry Discrimination at Transition States," 1993, Tetrahedron Letters, vol. 34, No. 3, pp. 403–406.

Jezowska–Bojczuk, et al., "Copper(II) Interactions with an Experimental Antiviral Agent, 1–Deoxynojirimycin, and Oxygen Activation by Resulting Complexes," 1996, Journal of Inorganic Biochemistry, vol. 64, pp. 231–246.

Ramu, et al., "Differences in Lipid Composition of Doxorubicin–Sensitive and –Resistant P388 Cells," Apr. 1984, Cancer Treatment Reports, vol. 68, No. 4, pp. 637–641.

Beketic–Oreskovic, et al., "Decreased Mutation Rate for Cellular Resistance to Doxorubicin and Suppression of mdr1 Gene Activation by the Cyclosporin PSC 833," Nov. 1, 1995, Journal of the National Cancer Institute, vol. 87, No. 21, pp. 1593–1602.

Coates, et al., "Developments in Viral Hepatitis During 1994," 1995, Exp. Opin. Ther. Patents, 5(8): 747–756.

Korba, et al., "Effectiveness of Combination Therapies with 3TC, Famciclovir, and Alpha Interferon Against Woodchuck Hepatitis Virus Replication in Chronically–infected Woodchucks: Model for Potential Anti–HBV Treatments," Apr. 1997, Antiviral Research, vol. 34, No. 2, p. A52.

Volm, et al., "Expression of Resistance Factors (P–Glycoprotein, Glutathione S–Transferase–II, and Topoisomerase II) and Their Interrlationship to Proto–Oncogene Products in Renal Cell Carcinomas," Jun. 15, 1993, Cancer, vol. 71, No. 12, pp. 3981–3987.

Lu, et al., "Evidence That N–Linked Glycosylation is Necessary for Hepatitis B Virus Secretion," Nov. 10, 1995, Virology, vol. 213, No. 2, pp. 660–665.

Wiltink, "Future Prospects in Antiviral Therapy," Jun. 1992, Pharmaceutisch Weekblad Scientific Edition, 14(4A), pp. 268–274.

Hardman, et al., "Goodman & Gilman's The Pharmacological Basis of Therapeutics," 1996, McGraw–Hell, Ninth Edition, Chapter 32: Drugs Used for the Treatment of Myocardial Ischemia, Verepemil, pp. 767–774, 780–781, 799–801, and 829.

Mehta, et al., "Hepatitis B Virus (HBV) Envelope Glycoproteins Vary Drastically in Their Sensitivity to Glycan Processing: Evidence that Alteration of a Single N–Linked Glycosylation Site Can Regulate HBV Secretion," Mar. 1997, Proc. Natl. Acad. Sci., vol. 94, pp. 1822–1827.

Locarnini, et al., "Hepatitis B: New Approaches to Antiviral Chemotherapy," 1996 Antiviral Chemistry & Chemotherapy, 7(2), pp. 53–64.

Hollinger, "Hepatitis B Virus," Field Virology, Third Edition, Chapter 86, pp. 2739–2807, 1992.

Doong, et al., "Inhibition of the Replication of Hepatitis B Virus In Vitro by 2',3'–dideoxy–3'–thiacytidine and Related Analogues," Oct. 1991, Proc. Natl. Acad. Sci., vol. 88, pp. 8495–8499.

Fleet, et al., "Inhibition of HIV Replication by Amino–Sugar Derivatives," Sep. 1988, Federation of European Biochemical Societies, vol. 237, No. 1,2, pp. 128–132.

Newbrun, et al., "Inhibition by Acarbose, Nojirimycin and 1–Deoxynojirimycin of Glucosyltransferase Produced by Oral Streptococci," 1983, Archs Oral Biol., vol. 28, No. 6, pp. 531–536.

Saunier, et al., "Inhibition of N–Linked Complex Oligosaccharide Formation by 1–Deoxynojirimycin, An Inhibitor of Processing Glucosidases," Dec. 10, 1982, The Journal of Biological Chemistry, vol. 257, No. 23, pp. 14155–14161.

Tan, et al., "Introduction of Oxygen into the Alkyl Chain of N–decyl–dNM Decreases Lipophilicity and Results in Increased Retention of Glucose Residues on N–Linked Oligosaccharides," 1994, Glycobiology, vol. 4, No. 2, pp. 141–149.

Elbein, "Inhibitors of the Biosynthesis and Processing of N–Linked Oligosaccharide Chains," 1987, Ann. Rev. Biochem., 56:497–534.

Korba, "In Vitro Evaluation of Combination Therapies Against Hepatitis B Virus Replication," 1995, Antiviral Research, vol. 29, pp. 49–51.

Bradley, et al., "Mechanism of Multidrug Resistance," 1988, Biochimica et Biophysica Acta, vol. 948, pp. 87–128.

Mülder, et al., "Multidrug Resistance–Modifying Components in Human Plasma with Potential Clinical Significance," Jan. 1996, Journal of Experimental Therapeutics & Oncology, vol. 1, No. 1, pp. 13–22.

Ardalan, et al., "Mechanism of Action of a New Antitumor Agent, Carbetimer," Nov. 1986, Cancer Research, vol. 46, pp. 5473–5476.

Platt, et al., "Modulation of Cell–Surface Transferrin Receptor by the Imino Sugar N–butyldeoxynojirimycin," 1992, Eur. J. Biochem., vol. 208, pp 187–193.

Kawakami, et al., "Monoclonal Antibodies with Affinity to Self–Complementary Left–Handed DNA Containing Cyclonucleosides with High Anti Conformation," 1994, Nucleosides & Nucleotides, vol. 13(1–3), pp. 421–427.

Carbohydrate Chemistry, "Chapter 20: Nucleotides," vol. 27, 1993, pp. 242–276.

Platt, et al., "N–Butyldeoxynojirimycin Is a Novel Inhibitor of Glycolipid Biosynthesis: Secretion of Human Hepatitis B Virus Is Inhibited by the Imino Sugar N–Butyldeoxynojirimycin," 1994, Chemtracts—Organic Chemistry, vol. 7, pp. 106–107.

Wilson, et al., "Nitrogen Glycosylation Reactions Involving Pyrimidine and Purine Nucleoside Bases with Furanoside Sugars," Dec. 1995, Synthesis, Department of Chemistry, Emory University, pp. 1465–1479.

Kers, et al., "Nucleoside Phosphonates. Development of Synthetic Methods and Reagents," 1996, Nucleosides & Nucleotides, 15(1–3), pp. 361–378.

Tsuruo, et al., "Overcoming of Vincristine Resistance in P388 Leukemis In Vivo and In Vitro Enhanced Cytotoxicity of Vincristine and Vinblastine by Verapamil," May 1981, Cancer Research, vol. 41, pp. 1967–1972.

Wright, et al., "Phospholipid and Ether Linked Phospholipid Content Alter with Cellular Resistance to Vinblastine," Dec. 17, 1985, Biochemical and Biophysical Research Communications, vol. 133, No. 2, pp. 539–545.

Bradley, et al., "P–glycoprotein, Multidrug Resistance and Tumor Progression," 1994, Cancer and Metastasis Reviews, vol. 13, pp. 223–233.

May, et al., "Plasma Membrane Lipid Composition of Vinblastine Sensitive and Resistant Human Leukaemic Lymphoblasts," 1988, Int. J. Cancer, vol. 42, pp. 728–733.

Mutchnick, et al., "Prospectives on the Treatment of Chronic Hepatitis B and Chronic Hepatitis C with Thymic Peptides and Antiviral Agents," 1994, Antiviral Research, vol. 24, pp. 245–257.

Wishart, et al., "Quinidine as a Resistance Modulator of Epirubicin in Advanced Breast Cancer: Mature Results of a Placebo–Controlled Randomized Trial," Sep. 1994, Journal of Clinical Oncology, vol. 12, No. 9, pp. 1771–1777.

Chabner, et al., "Reversal of Multidrug Resistance," Jan. 1991, Journal of Clinical Oncology, vol. 9, No. 1, pp. 4–6.

Hui, et al., "Reduced $p21^{WAF1/CIP1}$ Expression and p53 Mutation in Hepatocellular Carcinomas," Mar. 1997, Hepatology, vol. 25, No. 3, pp. 575–579.

Arends, "Recueil des Travaux Chimiques des Pays–Bas," Journal of the Royal Netherlands Chemical Society, Feb. 1994, Recl. Trav. Chim. Pays–Bas 113, 63–114, contents page only.

Rosina, et al., "Recent Developments in the Treatment of Hepatitis D Infection," 1996, Anti–infectives—Section Review, Exp. Opin. Invest. Drugs, No. 5(2), pp. 197–205.

Gish, et al., "Recent Developments in the Treatment of Chronic Hepatitis B Virus Infection," 1995, Exp. Opin. Invest. Drugs, 4(2), pp. 95–115.

Block, et al., "Secretion of Human Hepatitis B Virus is Inhibited by the Imino Sugar N–butyldeoxynojirimycin," Mar. 1994, Proc. Natl. Acad. Sci., vol. 91, pp. 2235–2239.

Vorbrüggen, et al., "Some Recent Trends and Progress in Nucleoside Synthesis," 1996, Acta Biochimica Polonica, vol. 43, No. 1, pp. 25–36.

Sobrero, et al., "Sequential Dichloromethotrexate (DCM) and 5–Fluorouracil (FU): A Synergistic Combination Potentially Valuable for Hepatic Artery Infusion Therapy," Mar. 1983, ASCO Abstracts, Clinical Pharmacology, vol. 2, Article C–102, p. 26.

van den Broek, et al., "Synthesis of Oxygen–Substituted N–alkyl 1–deoxynojirimycin derivates: aza sugar α–glucosidase inhibitors showing antiviral (HIV–1) and immunosuppressive activity," Recl. Trav. Chim. Pays–Bas 113, 1994, pp. 507–516.

Wadkins, et al., "The Role of Drug–Lipid Interactions in the Biological Activity of Modulators of Multi–Drug Resistance," 1993, Biochimica et Biophysica Acta, vol. 1153, pp. 225–236.

Doige, et al., "The Effects of Lipids and Detergents on ATPase–Active P–Glycoprotein," 1993, Biochimica et Biophysica Acta, vol. 1146, pp. 65–72.

Ries, et al., "Treatment of Advanced and Refractory Breast Cancer with Doxorubicin, Vincristine and Continuous Infusion of Verapamil. A Phase I–II Clinical Trial," 1991, Med. Oncol. & Tumor Pharmacother, vol. 8, No. 1, pp. 39–43.

Dusheiko, "Treatment and Prevention of Chronic Viral Hepatitis," 1995, Pharmac. Ther., vol. 65, pp. 47–73.

Block, et al., "Treatment of Chronic Hepadnavirus Infection in a Woodchuck Animal Model with an Inhibitor of Protein Folding and Trafficking," May 1998, Nature Medicine, vol. 4, No. 5, pp. 610–614.

Repp, et al., "The Effects of Processing Inhibitors of N–Linked Oligosaccharides on the Intracellular Migration of Glycoprotein E2 of Mouse Hepatitis Virus and the Maturation of Coronavirus Particles," Dec. 15, 1986, The Journal of Biological Chemistry, vol. 260, No. 29, pp. 15873–15879.

Block, et al., "The Secretion of Human Hepatitis B Virus is Inhibited by the Imino Sugar, N–Butyl–Deoxynojirimycin," undated, Jefferson Cancer Institute, et al., No. 81, one page, 1993.

Mutchnick, et al., "Thymosin Treatment of Chronic Hepatitis B: A Placebo–controlled Pilot Trial," 1991, Hepatology, vol. 14, No. 3, pp. 409–415.

Simon, et al., "Treatment of Chronic Hepatitis C with Interferon Alfa–n3: A Multicenter, Randomized, Open–Label Trial," Feb. 1997, Hepatology, vol. 25, No. 2, pp. 445–448.

Hoofnagle, et al., "The Treatment of Chronic Viral Hepatitis," Drug Therapy, vol. 336, No. 5, pp. 347–356, 1994.

Rhodes, et al., "Therapeutic Potential of Schiff Base–forming Drugs," 1996, Exp. Opin. Invest. Drugs, 5(3), pp. 257–268.

Lindsay, et al., "Thymosin $\alpha_1$ Treatment of Chronic Hepatitis B: A Multicenter, Randomized, Placebo–Controlled Double Blind Study," Apr. 1995, AASLD, A1127, one page.

Mutchnick, et al., "Thymosin Treatment of Chronic Active Hepatitis B (CAHB): A Preliminary Report on a Controlled, Double Blind Study," 1988, Hepatology, vol. 8, No. 5, Article 208, p. 1270.

Dwek, Raymond, "Glycobiology: Toward Understanding the Function of Sugars," Chem. Rev. 1996, 96, pp. 683–720.

Platt, Frances M., et al., "Inhibitors of Glycosphingolipid Biosynthesis," Trends in Glycoscience and Glycotechnology, vol. 7, No. 38, Nov. 1995, pp. 495–511.

Mutchnick, et al., "Thymosin Treatment of Chronic Active Hepatitis B (CAHB): Results of Pilot Study," Hepatology, vol. 10, No. 4, 1989.

Abe, Akira et al., "Improved Inhibitors of Glucosylceramide Synthase," *J. Biochem.*, vol. 111, No. 2, pp. 191–196 (1992).

Abe, Akira et al., "Structural and stereochemical studies of potent inhibitors of glucosylceramide synthase and tumor cell growth," *Journal of Lipid Research*, vol. 36, pp. 611–621 (1995).

Abe, Akira et al., "Induction of glucosylceramide synthase by synthase inhibitors and ceramide," *Biochimica et Biophysica Acta*, 1299, pp. 333–341 (1996).

Bolhuis, Henk et al., "Mechanisms of mutlidrug transporters," *FEMS Microbiology Reviews*, 21, pp. 54–84, 1997.

Cabot, Myles C., et al., "Tamoxifen retards glycosphingolipid metabolism in human cancer cells," *FEBS Letters*, 394, pp. 129–131 (1996).

Dicato, Mario et al., "Multidrug resistance: molecular and clinical aspects," *Cytokines, Cellular & Molecular Therapy*, vol. 3, No. 2, pp. 91–100, 1997.

Fischl, Margaret A., et al., "The Safety and Efficacy of Combination N–Butyl–Deoxynojirimycin (SC–48334) and Zidovudine in Patients with HIV–1 Infection and 200–500 CD4 Cells/$mm^3$," *Journal of Acquired Immune Deficiency Syndromes*, vol. 7, No. 2, pp. 139–147, 1994.

Inokuchi, Jin–ichi, et al., "Antitumor Activity Via Inhibition Of Glycosphingolipid Biosynthesis," *Cancer Letters*, 38, pp. 23–30, 1987.

Inokuchi, Jin–ichi, et al., "Stimulation of Glycosphingolipid Biosynthesis by L–Threo–1–Phenyl–2–Decanoylamino–1–Propanol and Its Homologs in B16 Melanoma Cells," *J. Biochem.*, vol. 117, No. 4, pp. 766–773, 1995.

Lavie, Yaakov et al., "Accumulation of Glucosylceramides in Multidrug–resistant Cancer Cells," *The Journal of Biological Chemistry*, vol. 271, No. 32, pp. 19530–19536, 1996.

Lavie, Yaakov et al., "Agents that Reverse Multidrug Resistance, Tamoxifen, Verapamil, and Cyclosporin A, Block Glycosphingolipid Metabolism by Inhibiting Ceramide Glycosylation in Human Cancer Cells," *The Journal of Biological Chemistry*, vol. 272, No. 3, pp. 1682–1687, 1997.

Legler, Günter et al., "Glucosylceramidase from Calf Spleen," *Biol. Chem. Hoppe–Seyler*, vol. 366, pp. 1113–1122, 1985.

Ogawa, Seiichiro et al., "Synthesis of Potent β–D–Glucocerebrosidase Inhibitors: N–Alkyl–β–Valienamines," *Bioorganic & Medicinal Chemistry Letters*, vol. 6, No. 8, pp. 929–932, 1996.

Platt, Frances et al., "New Approach for the Treatment of Gauchers Disease," *Gauchers Association Newsletter*, p. 8, 1996.

Platt, Frances M., et al., "N–Butyldeoxynojirimycin Is a Novel Inhibitor of Glycolipid Biosynthesis," *The Journal of Biological Chemistry*, vol. 269, No. 11, pp. 8362–8365, 1994.

Platt, Frances M., et al., N–Butyldeoxygalactonojirimycin Inhibits Glycolipid Biosynthesis but Does Not Affect N–Linked Oligosaccharide Processing, *The Journal of Biological Chemistry*, vol. 269, No. 43, pp. 27108–27114, 1994.

Platt, Frances M., et al., "Prevention of Lysosomal Storage in Tay–Sachs Mice Treated with N–Butyldeoxynojirimycin," *Science*, vol. 276, pp. 428–431, 1997.

Prence, E. M., et al., "In Vitro Accumulation of Glucocerebroside in Neuroblastoma Cells: A Model for Study of Gaucher Disease Pathobiology," *Journal of Neuroscience Research*, 43, pp. 365–371, 1996.

Radin, Norman S., et al., "Inhibitors of Cerebroside Metabolism," *Methods in Enzymology*, vol. 72, pp. 673–684, 1981.

Radin, Norman S., Rationales for Cancer Chemotherapy with PDMP, a Specific Inhibitor of Glucosylceramide Synthase, *Molecular and Chemical Neuropathology*, vol. 21, pp. 111–127, 1994.

Radin, Norman S., "Treatment of Gaucher disease with an enzyme inhibitor," *Glycoconjugate Journal*, 13, pp. 153–157, 1996.

Shukla, Girja S., et al., "Rapid kidney changes resulting from glycosphingolipid depletion by treatment with a glucosyltransferase inhibitor," *Biochimica et Biophysica Acta*, 1083, pp. 101–108, 1991.

Lavie et al., "Acculmulation of Glucosylceramides in Multidrug–resistant Cancer Cells", Journal of Biological Chemistry, vol. 271, No. 32, pp. 19530–19536, Aug. 1996.*

Platt et al., "N–Butyldeoxygalactonojirimycin Inhibits Glycolipid Biosynthesis but Does Not Affect N–Linked Oligosaccharide Processing", Journal of Biological Chemistry, vol. 259, No. 43, pp. 27108–27114, Oct. 1994.*

Yangco, B., et al., Pilot Safety and Efficacy of Combination SC–48334 (N–Butyl–Deoxynojirimycin [NB–DNJ]and Zidovudine (ZDV) in Symptomatic HIV–1 Infected Patients with>=200 –<=500 CD4 Cells/mm3, Abstracts of the 1st National Conf. on Human Retroviruses, Session 86, No. 574 ( ABSTRACT).

Fischl, M., et al., The Preliminary Efficacy and Safety of N–Butyl Deoxynojirimycin (SC–48334), an alpha–Glucosidase 1 Inhibitor, in Combination with Ziduvudine (ZDV), International Conference on Aids IXth (9th) International Conference on Aids in affiliation with the IVth (4th) STD World Congress, Berlin, Jun. 6–11th, 1993.

Ratner, L., et al., Mechanism of Action of N–Butyl Deoxynojirimycin in Inhibiting HIV–1 Infection and Activity in Combination with Nucleoside Analogs, Aids Research and Human Retroviruses, vol. 9, No. 4, 1993, pp. 291–297.

Myers, M.W., New Antiretroviral Agents in the Clinic, Reviews of Infectious Diseases, vol. 12, No. 5, Sep.–Oct. 1990, pp. 944–950.

Acosta, E.P. et al., Agents for Treating Human Immunodeficiency Virus Infection, American Journal of Hospital Pharmacy, vol. 51, No. 18, Sep. 15, 1994, pp. 2251–2287.

Gasparini, G et al., Cinical Importance of the Determination of Tumor Angiogenesis in Breast Carcinoma: Much More Than a New Prognostic Tool, Journal of Clinincal Oncology, The Official Journal of the American Society of Clinical Oncology, vol. 13, No. 3, Mar. 1995, pp. 765–782.

Jacob, G.S., Glycosylation Inhibitors in Biology and Medicine, Current Opinion in Structural Biology, vol. 5, 1995, pp. 605–611.

Goss, P.E., et al., Inhibitors of Carbohydrate Processing: A New Class of Anticancer Agents, Clinical Cancer Research , vol. 1, No. 9, pp. 935–944.

Jacob, G.S., et al., Iminosugar alpha–Glucosidase Inhibitors as Drugs and Pro–Drugs for Treatment of HIV Infections (Abstract No. 12), Washington Book of Abstracts, 208th ACS National Meeting, Aug. 21–25, 1994.

Azidothymidine Archives of Internal Medicine, vol. 152, No. 3, Mar. 1992, pp. 485–501.

Sachs, M.K., Antiretroviral Chemotherapy of Human Immunodeficiency Virus Infections Other Than With Azidothymidine, Archives of Internal Medicine, vol. 152, No. 3, Mar. 1992, pp. 485–501.

Isom, H.C., et al., Molecular Pathology of Human Oncogenic Viruses, Cellular and Molecular Pathogenesis, edited by A.E. Sirica, Lippincott–Raven Publishers, Philadelphia, 1996, pp. 341–387.

Fiume, L., et al., Targeting of Antiviral Drugs to the Liver Using Glycoprotein Carriers, Advanced Drug Delivery Reviews, vol. 14, No. 1, Apr.–May, 1994, pp. 51–65.

Rusconi, S., et al., Inhibition of Human Immunodeficiency Virus Type 1 Replication in Cytokine–Stimulated Monocytes/Macrophages by Combination Therapy, The Journal of Infections Diseases, vol. 170, No. 6, Dec. 1994, pp. 1361–1366.

Molecular Medicine, vol. 33, No. 3, 1996, pp. 276–286 (English abstract).

Bruyneel, E.A., et al., Effect of Glycosylation Inhibitors on N–glycosylpeptides and on Invasion of Malignant Mouse MO4 cells in vitro, Journal of Cell Science, vol. 95, 1990, pp. 279–286.

* cited by examiner

USE OF ALKYLATED IMINOSUGARS TO TREAT MULTIDRUG RESISTANCE

This application claims the benefit of priority of U.S. Provisional Application No. 60/065,051 filed Nov. 10, 1997.

BACKGROUND OF THE INVENTION

1. Field of the Invention

The present invention relates to the field of cancer chemotherapy. More particularly, the present invention relates to a method for improving the effectiveness of cancer chemotherapy by preventing, reducing, or reversing the development of cellular resistance to chemotherapeutic agents, i.e., the phenomenon known as "multidrug resistance" (MDR), during the course of therapy. This is achieved by administering to patients N-alkyl-1,5-dideoxy-1,5-imino-D-glucitol or galactitol compounds ("iminosugars") in conjunction with chemotherapeutic drugs.

2. Description of Related Art

Multidrug Resistance (MDR)

Multidrug resistance, the phenomenon whereby primary exposure of tumor cells to a single chemotherapeutic drug results in cellular resistance to multiple drugs, is believed to be the basis for tumor cell survival (Bradley et al. (1988) *Biochim. Biophys. Acta* 948:87–128). MDR is manifested as a simultaneously acquired cellular resistance to several cytotoxic substances, which can be surprisingly structurally and functionally unrelated, and is often observed after prolonged exposure of cells to anticancer drugs of the "multidrug resistance group." The latter includes such different compounds as actinomycin D, mitomycin C, anthracyclines, colchicine, rhodamine, ethidium bromide, doxorubicin, epipodophyllotoxins, paclitaxel, taxol, reserpine, and the vinca alkaloids. Exposure of cells to one of these drugs can lead not only to specific resistance to this drug, but also to non-specific cross-resistance to all the other drugs of the MDR group.

Study of this phenomenon has focused on a number of different possible biological mechanisms. Volm et al. ((1993) *Cancer* 71:2981–2987) and Bradley et al. ((1994) *Cancer Metastasis Rev.* 13:223–233) have investigated the overexpression of P-gp, a plasma membrane glycoprotein believed to rapidly efflux MDR-type drugs, thus protecting cells from damage by preventing these drugs from reaching their intracellular targets. Doige et al. ((1993) *Biochim. Biophys. Acta* 1146:65–72) and Wadkins et al. ((1993) *Biochim. Biophys. Acta* 1153:225–236) have studied the role of lipids in MDR. While differences in the glycerolipid and sphingomyelin compositions of MDR and drug-sensitive cells have been observed (Holleran et al. (1986) *Cancer Chemother. Pharmacol.* 17:11–15; Ramu et al. (1984) *Cancer Treat. Rep.* 68:637–641; May et al. (1988) *Int. J. Cancer* 42:728–733; Welsh et al. (1994) *Arch. Biochem. Biophys.* 315:41–47; Wright et al. (1985) *Biochem. Biophys. Res. Commun.* 133:539–545), and the ganglioside composition of MDR and drug-sensitive cells has been investigated, no clear picture as to the basis of drug resistance emerged from these studies.

More recently, Lavie et al. ((1996) *J. Biol. Chem.* 271:19530–10536) demonstrated a correlation between the cellular content of glycosphingolipids and MDR. These workers demonstrated that tamoxifen, verapamil, and cyclosporin A, agents that reverse multidrug resistance, as well as 1-phenyl-2-palmitoylamino-3-morpholino-1-propanol, an inhibitor of glucosylceramide synthesis, decrease glucosylceramide levels in an MDR human breast cancer cell line that accumulates high levels of glucosylceramide compared with the parental wild-type, drug-sensitive cell line (Lavie et al. (1997) *J. Biol. Chem.* 272:1682–1687). They concluded that high cellular levels of glucosylceramide are correlated with MDR, and that glycolipids are therefore a target for the action of MDR-reversing agents.

1,5-dideoxy-1,5-imino-D-glucitol and galactitol Compounds 1,5-dideoxy-1,5-imino-D-glucitol (also known as 1-deoxynojirimycin, DNJ) and its N-alkyl derivatives are known inhibitors of the N-linked oligosaccharide processing enzymes α-glucosidase I and II (Saunier et al., *J. Biol.Chem.* (1982) 257:14155–14161 (1982); Elbein, *Ann. Rev. Biochem.* (1987) 56:497–534). As glucose analogs, they were also predicted to have the potential to inhibit glucose transport, glucosyltransferases, and/or glycolipid synthesis (Newbrun et al., *Arch. Oral Biol.* (1983) 28: 516–536; Wang et al., *Tetrahedron Lett.* (1993) 34:403–406). Their inhibitory activity against glucosidases has led to the development of these compounds as anti-hyperglycemic agents and anti-viral agents. See, for example, PCT International Publication WO 87/03903 and U.S. Pat. Nos. 4,065,562; 4,182,767; 4,533,668; 4,639,436; 4,849,430; 4,957,926; 5,011,829; and 5,030,638. N-butyl DNJ is an inhibitor of HIV replication in vitro (Fleet et al. (1988) *FEBS Lett.* 237:128–132; Karpas et al. (1988) *Proc. Natl. Acad. Sci. USA* 85:9229–9233). This compound has been clinically evaluated as a potential AIDS therapeutic (Jacob et al. (1992) in *Natural Products as Antiviral Agents*, C. K. Chu et al., Eds., pp. 137–152, Plenum Publishing Co., N.Y.), and has been found to exhibit little cytotoxicity in vitro (Platt et al. (1992) *Eur. J. Biochem.* 208:187–193).

Platt et al. ((1994) J. Biol. Chem. 269:8362–8365) have demonstrated that certain N-alkylated derivatives of DNJ inhibit the glucosyltransferase-catalyzed biosynthesis of glucosylceramide, resulting in the inhibition of biosynthesis of all glucosylceramide-based glycosphingolipids. Glycolipids constitute an important class of glycoconjugates found in the membranes, and particularly the plasma membrane, of eukaryotic cells. These authors speculated that these N-alkylated derivatives specifically inhibit UDP-glucose-N-acylsphingosine glucosyltransferase (EC 2.4.1.80). This transferase generates glucosylceramide (GlcCer), the precursor for the more complex glycosphingolipids and gangliosides. Platt et al. also demonstrated that N-butyl DNJ inhibited glycolipid expression at the cell surface. The authors suggested that N-alkylated DNJs would be useful in treating lysosomal glycolipid storage disorders such as Gaucher's disease.

In a subsequent paper, Platt et al. showed that the galactose analogue of N-butyl DNJ, i.e., N-butyl-deoxygalactonojirimycin (N-butyl DGJ), is a more selective inhibitor of glycolipid biosynthesis, only weakly inhibiting the N-linked oligosaccharide processing enzymes α-glucosidases I and II, and not inhibiting lysosomal β-glucocerebrosidase (which is required for the cleavage of GlcCer to glucose and ceramide). N-butyl DGJ was shown to be comparable to N-butyl DNJ as an inhibitor of UDP-glucose-N-acylsphingosine glucosyltransferase and in preventing lysosomal glycolipid storage in an in vitro model of Gaucher's disease.

In 1997, Platt et al. (Science 276:428–431) reported the prevention of glycosphingolipid lysosomal storage in a mouse model of Tay-Sachs disease using N-butyl DNJ. This disease is characterized by a deficiency in the A isoenzyme of β-hexosaminidase, which degrades $G_{M2}$ ganglioside. A deficiency of this enzyme in humans results in accumulation of $G_{M2}$ ganglioside in brain cell lysosomes, leading to severe neurological degeneration. The authors noted that this compound is water soluble and noncytotoxic over a broad range of concentrations in vitro and in vivo. Oral administration to healthy mice resulted in glycosphingolipid depletion in multiple organs without causing any overt pathological side effects. In Tay-Sachs mice, no toxicity to N-butyl DNJ was observed based on visible inspection and observation of the animals, and of organ weights at autopsy. While spleen and thymus tissues were 50% acellular, no immunocompromization was apparent. The authors concluded that in this in vivo mammalian model, oral treatment with N-butyl DNJ is well tolerated, and effectively inhibits glycosphingolipid biosynthesis and subsequent accumulation in brain cell lysosomes.

Treatment of MDR

Many chemosensitizers have been reported to antagonize MDR in in vitro systems, and some have been shown to be effective in viva when coadministered with appropriate chemotherapeutic agents to nude mice bearing multidrug-resistant tumors. Unfortunately, success in the laboratory has not necessarily translated to success in the clinic. Dose-limiting side effects of first-generation MDR modulators have been observed. Low therapeutic indices and failure to achieve therapeutic blood levels have also been problematic (Dalton et al. (1995) *Cancer* 75:815–20; Tsuro et al. (1981) *Cancer Res.* 41:1967–72; Ries et al. (1991) *Med. Oncol. Tumor Pharmacother.* 9:39–42; Chabner (1991) *J. Clin. Oncol.* 9:4–6; Raderer et al. (1993) *Cancer* 72:3553–63; Mulder et al. (1996) *J. Exp. Ther. Oncol.* 1:19–28; Fischer et al. (1995) *Hematol. Oncol. Clin. North Am.* 9:363–82; Wishart et al. (1994) *J. Clin. Oncol.* 9:1771–77). In addition, patient dosing is sometimes complicated by pharmacokinetic drug interactions, resulting in increased plasma concentrations or decreased elimination of cytotoxic drugs, resulting in increased toxicity (Egorin et al. (1996) *Proc. Am. Soc. Clin. Oncol.* 15:473; Beketic-Oreskovic et al. (1995) *J. Natl. Cancer Inst.* 1593–602.88). Most of the results from MDR-reversal trials have been disappointing, except for those for some hematological cancers (Chabner (1991) *J. Clin. Oncol.* 9:4–6; Raderer et al. (1993) *Cancer* 72:3553–63; Mulder et al. (1996) *J. Exp. Ther. Oncol.* 1:19–28; Fischer et al. (1995) *Hematol. Oncol. Clin. North Am.* 9:363–82).

Thus, a common, major obstacle to cure with chemotherapeutic agents is the survival and continued proliferation of cells that are resistant to further treatment. MDR is therefore a formidable impediment to successful chemotherapy. The art continues to seek agents that can be used to prevent or reduce this phenomenon during cancer chemotherapy. The use of N-substituted-imino-D-glucitol or galactitol derivatives in conjunction with chemotherapeutic agents for preventing or reducing the extent of MDR during chemotherapy has not, as far as the present inventor is aware, been previously disclosed or suggested.

SUMMARY OF THE INVENTION

In response to the need of the healing arts for agents that can be used to avoid the deleterious consequences of MDR during chemotherapy, the present inventor has surprisingly discovered that certain iminosugar glucosylceramide synthase inhibitors are effective for this purpose. These inhibitors can be used to prevent, reduce, or reverse MDR often observed during treatment of cancer patients with chemical anti-cancer agents.

As noted above, first-generation MDR modulators exhibit a number of disadvantageous side effects. In addition, drugs such as verapamil, tamoxifen, cyclosporin A, and 1-phenyl-2-palmitoylamino-3-morpholino-1-propanol exhibit other, well known pharmacologic effects which may be undersirable in certain patients. In contrast, the iminosugars of the present invention possess beneficial advantages in treating MDR including, but not limited to, mechanistic specificity, lack of drug-drug interactions, and minimal or no effect on elimination of cytotoxic chemotherapeutic drugs.

Accordingly, in one aspect, the present invention provides a method for preventing, reducing, or reversing multidrug resistance in a patient undergoing treatment with a chemotherapeutic agent, comprising administering to the patient an anti-multidrug resistance effective amount of an N-substituted-1,5-dideoxy-1,5-imino-D-glucitol or galactitol compound, or pharmaceutically acceptable salt thereof, of Formula I:

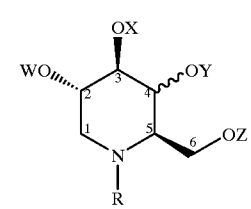

wherein R is selected from arylalkyl, cycloalkylalkyl, and branched or straight chain alkyl having a chain length of $C_2$ to $C_{20}$, and W, X, Y and Z are each independently selected from hydrogen, alkanoyl, aroyl, and trifluoroalkanoyl, for a period of time effective to prevent, reduce, or reverse multidrug resistance in cancer cells of the patient. Preferred compounds are those wherein R is n-butyl or n-hexyl.

In this method, the N-substituted-1,5-dideoxy-1,5-imino-D-glucitol or galactitol compound, or combinations thereof, can be administered in accordance with a variety of different regimens, including prior to administration of the chemotherapeutic agent; both prior to and simultaneously with administration of the chemotherapeutic agent; prior to, simultaneously with, and subsequently to administration of the chemotherapeutic agent; simultaneously with administration of the chemotherapeutic agent; prior to and subsequently to administration of the chemotherapeutic agent; or daily throughout the entire course of treatment with the chemotherapeutic agent.

In a preferred embodiment, the present method comprises administering about 1,000 mg/day to about 3,000 mg/day of N-(n-butyl)-1,5-dideoxy-1,5-imino-D-glucitol or galactitol or N- (n-hexyl) -1,5-dideoxy-1,5-imino-D-glucitol or galactitol, or a pharmaceutically acceptable salt thereof, daily throughout the course of administration of a chemotherapeutic agent selected from an anthracycline, an alkaloid, an anti-microtubule drug, a topoisomerase II inhibitor, and a DNA damaging agent. Administration of the N-alkylated iminosugar can commence about 14 days prior to administration of the chemotherapeutic agent.

In another aspect, the present invention provides a pharmaceutical composition, comprising an anti-multidrug resistance effective amount of at least one N-substituted-1,5-dideoxy-1,5-imino-D-glucitol or galactitol compound as above, an anti-tumor effective amount of at least one anti-tumor chemotherapeutic compound, and a pharmaceutically acceptable carrier.

Further scope of the applicability of the present invention will become apparent from the detailed description and drawings provided below. However, it should be understood that the following detailed description and examples, while indicating preferred embodiments of the invention, are given by way of illustration only since various changes and modifications within the spirit and scope of the invention will become apparent to those skilled in the art from this detailed description.

DETAILED DESCRIPTION OF THE INVENTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein, including the contents of the references cited within these primary references, are herein incorporated by reference in their entirety.

The present inventor has discovered that N-substituted-1,5-dideoxy-1,5-imino-D-glucitol and galactitol compounds used in conjunction with antineoplastic chemotherapeutic agents are effective in preventing the development of, reducing the extent of, or reversing MDR in patients receiving chemotherapy.

The present invention thus provides pharmaceutical compositions and methods for preventing or reducing MDR in humans and other mammals being treated with chemical antitumor compounds by administering one or more N-substituted-1,5-dideoxy-1,5-imino-D-glucitol or galactitol compounds to patients. The iminosugar and chemotherapeutic drugs of this invention can be provided to cells, tissues, or organs in vitro or in viva, or to a human or other mammalian patient, including domestic animals such as cats and dogs, either in separate pharmaceutically acceptable formulations, formulations containing more than one therapeutic agent, or by an assortment of single agent and multiple agent formulations. However administered, these drug combinations form an anti-MDR effective and chemotherapeutically effective amount of components. Administration of the present iminosugar and chemotherapeutic drugs to cells, tissues, or organs in vitro can be used as model experimental systems in which to investigate the phenomenon of MDR, with the goal of optimizing in vivo treatment therefor.

As used herein, the term "anti-MDR effective amount" refers to an amount of an N-substituted-1,5-dideoxy-1,5-imino-D-glucitol or galactitol compound, or combination thereof, effective in preventing the development of, reducing the extent of, or reversing multidrug resistance often observed in tumor cells of patients being treated with antineoplastic agents. Such effective amount is medically beneficial, and does not cause toxic effects that outweigh the advantages associated with the use of these N-substituted-1,5-dideoxy-1,5-imino-D-glucitol or galactitol compounds in overcoming the adverse effects of MDR. The ultimate result is enhanced effectiveness of the chemotherapy.

Also as used herein, the term "multidrug resistance group" refers to those antineoplastic agents to which tumor cells develop resistance after exposure thereof to an anticancer chemotherapeutic compound, i.e., to which such tumor cells develop multidrug resistance, whether this be specific resistance to this particular anticancer chemotherapeutic compound, or non-specific cross-resistance to other chemotherapeutic compounds which may or may not be structurally and functionally related.

N-substituted-1,5-dideoxy-1,5-imino-D-glucose and Galactose Compounds

N-substituted-1,5-dideoxy-1,5-imino-D-glucitol or galactitol compounds useful in the present invention are represented by formula I:

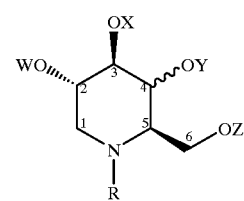

The glucitol and galactitol stereoisomers encompassed by formula I differ in the orientation of the hydroxyl group on C-4 of the ring. Employing the convention of Fleet et al. ((1992) *Glycobiology* 2:199–210), the ring in formula I lies flat in the plane of the page. A group attached to the ring via a bond depicted with a series of dashed lines is oriented below the plane of the ring; a group attached to the ring via a bond depicted with a solid, elongated triangle is oriented above the plane of the ring. The group attached to the ring at C-4 via the bond depicted by the squiggly line is either below the plane of the ring (glucitol derivatives) or above the plane of the ring (galactitol derivatives).

In formula I, R is selected from arylalkyl, cycloalkylalkyl, and branched or straight chain alkyl having a chain length of $C_2$ to $C_2$, preferably $C_4$ to $C_{20}$, more preferably $C_4$ to $C_{14}$, more preferably $C_4$ to $C_{10}$, more preferably $C_4$ to $C_8$, and most preferably $C_4$ to $C_6$ in the principal chain. n-butyl and n-hexyl are preferred.

R can also be $C_1$ to $C_{20}$ alkyl, preferably $C_2$ to $C_{14}$, more preferably $C_6$ to $C_{12}$, more preferably $C_4$ to $C_{10}$ alkyl, containing 1 to 5, more preferably 1 to 3, most preferably 1 to 2, oxygen atoms, i.e., oxa derivatives. Preferred R oxa derivatives are 3-oxanonyl, 3-oxadecyl, 7-oxanonyl, and 7-oxadecyl.

W, X, Y and Z are independently selected from hydrogen, alkanoyl, aroyl, and trifluoroalkanoyl.

As used herein, the term "alkyl" as used in "arylalkyl" and "cycloalkylalkyl," either unsubstituted or containing the various substituents defined herein, can contain from one to about six carbon atoms in the principal chain, and up to about 15 carbon atoms total. Such alkyl groups include, for example, methyl, ethyl, propyl, isopropyl, butyl, hexyl, cyclopropyl, cyclopentyl, cyclohexyl, and the like. Substituents of the substituted alkyl groups described herein can include, for example, groups selected from alkyl, cycloaklyl, alkenyl, alkynyl, aryl, heteroaryl, O, S, N, P, or halogen (Cl, P, Br, or I) atoms. Optionally, these substituent alkyl, cycloalkyl, etc., groups can be substituted with O, S, N, P, or halogen (Cl, F, Br, or I) atoms. These substituent alkyl, cycloakyl, etc., groups include, for example, lower alkoxy groups such as methoxy, ethoxy, and butoxy, and groups such as halo, nitro, amino, and keto.

The alkenyl groups described herein, either unsubstituted or with the various substituents defined herein, are preferably lower alkenyl groups containing from about two to about six carbon atoms in the principal chain, and up to about 15 carbon atoms total. They can be substituted, straight, or branched chain, and include ethenyl, propenyl, isopropenyl, butenyl, isobutenyl, hexenyl, and the like.

The alkynyl groups described herein, either unsubstituted or with the various substituents defined herein, are preferably lower alkynyl groups containing from about two to about six carbon atoms in the principal chain, and up to about 15 carbon atoms total. They can be substituted, straight or branched chain, and include ethynyl, propynyl, butynyl, isobutynyl, hexynyl, and the like.

The aryl moieties described herein, either unsubstituted or with various substituents defined herein, can contain from about 6 to about 15 carbon atoms, and include phenyl and naphthyl. Substituents include alkanoxy, protected hydroxy, halogen, alkyl, aryl, alkenyl, acyl, acyloxy, nitro, amino, amido, etc. Phenyl is a preferred aryl.

The cycloalkyl moieties described herein, either unsubstituted or with various substituents defined herein, can contain from about 5 to about 15 atoms, and include cyclobutylbutyl, cyclohexylhexyl, and the like. Substituents include alkanoxy, protected hydroxy, halogen, alkyl, aryl, alkenyl, acyl, acyloxy, nitro, amino, and amido.

The alkanoyl groups, either unsubstituted or substituted with the various substituents defined hereinabove for "alkyl" groups, and the trifluoroalkanoyl groups described herein, can contain from one to about six carbon atoms in the principal chain, and up to about 15 carbon atoms total, and include acetyl, propanoyl, butanoyl, and the like. The aroyl groups described herein, either unsubstituted or with various substituents defined herein, can contain from about 6 to about 15 carbon atoms, and include benzoyl. Substituents include alkanoxy, protected hydroxy, halogen, alkyl, aryl, alkenyl, acyl, acyloxy, nitro, amino, amido, etc. Benzoyl is a preferred aroyl.

The carbon atoms, i.e., the methyl and methylene groups, constituting the principal backbone of the branched or straight chain alkyl groups having a chain length of $C_2$ to $C_{20}$ can also be substituted as variously described above.

Representative N-substituted-imino-D-glucitol and galactitol compounds useful in the present invention include, but are not limited to:

N-(n-ethyl-)-15-dideoxy-1,5-imino-D-glucitol or galactitol;
N-(n-propyl-)-1,5-dideoxy-1,5-imino-D-glucitol or galactitol;
N-(n-butyl-)-1,5-dideoxy-1,5-imino-D-glucitol or galactitol;
N-(n-hexyl-)-1,5-dideoxy-1,5-imino-D-glucitol or galactitol;
N-(n-heptyl-)-1,5-dideoxy-1,5-imino-D-glucitol or galactitol;
N-(n-octyl-)-1,5-dideoxy-1,5-imino-D-glucitol or galactitol;
N-(n-octyl-)-1,5-dideoxy-1,5-imino-D-glucitol or galactitol, tetrabutyrate;
N-(n-nonyl-)-1,5-dideoxy-1,5-imino-D-glucitol or galactitol, tetrabutyrate;
N-(n-decyl-)-1,5-dideoxy-1,5-imino-D-glucitol or galactitol, tetrabutyrate;
N-(n-undecyl-)-1,5-dideoxy-1,5-imino-D-glucitol or galactitol, tetrabutyrate;
N-(n-nonyl-)-1,5-dideoxy-1,5-imino-D-glucitol or galactitol;
N-(n-decyl-)-1,5-dideoxy-1,5-imino-D-glucitol or galactitol;
N-(n-undecyl-)-1,5-dideoxy-1,5-imino-D-glucitol or galactitol;
N-(n-dodecyl-)-1,5-dideoxy-1,5-imino-D-glucitol or galactitol;
N-(2-ethylhexyl)-1,5-dideoxy-1,5-imino-D-glucitol or galactitol;
N-(4-ethylhexyl)-1,5-dideoxy-1,5-imino-D-glucitol or galactitol;
N-(5-methylhexyl)-1,5-dideoxy-1,5-imino-D-glucitol or galactitol;
N-(3-propylhexyl)-1,5-dideoxy-1,5-imino-D-glucitol or galactitol;
N-(1-pentylpentylhexyl)-1,5-dideoxy-1,5-imino-D-glucitol or galactitol;
N-(1-butylbutyl)-1,5-dideoxy-1,5-imino-D-glucitol or galactitol;
N-(7-methyloctyl-)-1,5-dideoxy-1,5-imino-D-glucitol or galactitol;
N-(8-methylnonyl)-1,5-dideoxy-1,5-imino-D-glucitol or galactitol;
N-(9-methyldecyl)-1,5-dideoxy-1,S-imino-D-glucitol or galactitol;
N-(10-methylundecyl)-1,5-dideoxy-1,5-imino-D-glucitol or galactitol;
N-(6-cyclohexylhexyl-)-1,5-dideoxy-1,5-imino-D-glucitol or galactitol;
N-(4-cyclohexylbutyl)-1,5-dideoxy-1,5-imino-D-glucitol or galactitol;
N-(2-cyclohexylethyl)-1,5-dideoxy-1,5-imino-D-glucitol or galactitol;
N-(1-cyclohexylmethyl)-1,5-dideoxy-1,5-imino-D-glucitol or galactitol;
N-(1-phenylmethyl)-1,5-dideoxy-1,5-imino-D-glucitol or galactitol;
N-(3-phenylpropyl)-1,5-dideoxy-1,5-imino-D-glucitol or galactitol;
N-(3-(4-methyl)-phenylpropyl)-1,5-dideoxy-1,5-imino-D-glucitol or galactitol;
N-(6-phenylhexyl)-1,5-dideoxy-1,5-imino-D-glucitol or galactitol;
N-(n-nonyl-)-1,5-dideoxy-1,5-imino-D-glucitol or galactitol, tetrabutyrate;
N-(n-decyl-)-1,5-dideoxy-1,5-imino-D-glucitol or galactitol, tetrabutyrate;
N-(n-undecyl-)-1,5-dideoxy-1,5-imino-D-glucitol or galactitol, tetrabutyrate;
N-(n-dodecyl-)-1,5-dideoxy-1,S-imino-D-glucitol or galactitol, tetrabutyrate;
N-(2-ethylhexyl)-1,5-dideoxy-1,5-imino-D-glucitol or galactitol, tetrabutyrate;
N-(4-ethylhexyl)-1,5-dideoxy-1,5-imino-D-glucitol or galactitol tetrabutyrate;
N-(5-methylhexyl)-1,5-dideoxy-1,5-imino-D-glucitol or galactitol, tetrabutyrate;
N-(3-propylhexyl)-1,5-dideoxy-1,5-imino-D-glucitol or galactitol, tetrabutyrate;
N-(1-pentylpentylhexyl)-1,5-dideoxy-1 5-imino-D-glucitol or galactitol, tetrabutyrate;
N-(1-butylbutyl)-1,5-dideoxy-1,5-imino-D-glucitol or galactitol, tetrabutyrate;
N-(7-methyloctyl-)-1,5-dideoxy-1,5-imino-D-glucitol or galactitol, tetrabutyrate;
N-(8-methylnonyl)-1,5-dideoxy-1,5-imino-D-glucitol or galactitol, tetrabutyrate;
N-(9-methyldecyl)-1,5-dideoxy-1,5-imino-D-glucitol or galactitol, tetrabutyrate;
N-(10-methylundecyl)-1,5-dideoxy-1,5-imino-D-glucitol or galactitol, tetrabutyrate;
N-(6-cyclohexylhexyl-)-15-dideoxy-1,5-imino-D-glucitol or galactitol, tetrabutyrate;
N-(4-cyclohexylbutyl)-1,5-dideoxy-1,5-imino-D-glucitol or galactitol, tetrabutyrate;
N-(2-cyclohexylethyl)-1,5-dideoxy-1,5-imino-D-glucitol or galactitol, tetrabutyrate;
N-(1-cyclohexylmethyl)-1,5-dideoxy-1,5-imino-D-glucitol or galactitol, tetrabutyrate;
N-(1-phenylmethyl)-1,5-dideoxy-1,5-imino-D-glucitol or galactitol, tetrabutyrate;
N-(3-phenylpropyl)-1,5-dideoxy-1,5-imino-D-glucitol or galactitol, tetrabutyrate;

N-(3-(4-methyl)-phenylpropyl)-1,5-dideoxy-1,5-imino-D-glucitol or galactitol, tetrabutyrate; and N-(6-phenylhexyl)-1,5-dideoxy-1,5-imino-D-glucitol or galactitol, tetrabutyrate.

Pharmaceutically acceptable salts of any of the glucitol or galactitol compounds encompassed herein can also be used in the methods of the present invention.

Preferred compounds are N-(n-butyl-) -1,5-dideoxy-1,5-imino-D-glucitol or galactitol and N-(n-hexyl-)-1,5-dideoxy-1,5-imino-D-glucitol or galactitol.

The N-substituted-imino-D glucitol compounds useful in the present invention can be prepared by methods well known in the art as described in, for example, Fleet et al. (1988) FEBS Lett. 237:128–132, U.S. Pat. Nos. 4,182,767, 4,639,436, and 5,003,072, as well as PCT International Publication WO 95/19172 and the references cited therein. Deoxynojirimycin (DNJ) can be obtained from Sigma Chemical Company (St. Louis; cat. no. D 3291).

N-substituted-imino-D-galactitol compounds can be prepared from deoxygalactonojirimycin (DGJ), which can be obtained from Cambridge Research Biochemicals (Northwich, Cheshire, U.K.), as described in Platt et al. (1994) J. Biol. Chem. 269:27108–27114. Briefly, DGJ can be reductively N-alkylated in the presence of palladium black under hydrogen using the appropriate aldehyde by the method of Fleet et al. (1988) FEBS Lett. 237:128–132. The reaction mixture is filtered through Celite, and the solvent removed by evaporation under vacuum. The resulting N-alkylated analogues are then purified by ion-exchange chromatography (Dowex® AG50-X12, H+ form) in 2M aqueous ammonia, and the solvent removed by evaporation. The compounds can then be lyophilized and analyzed by 1D $^1$H NMR and by matrix-assisted laser desorption.

Methods for introducing oxygen into alkyl side chains are disclosed in Tan et al., (1994) Glycobiology 4(2):141–149.

Non-limiting illustrative preparative procedures are presented below in Examples 1–5.

In treating MDR, the medical practitioner can use the N-substituted-imino-D-glucitol or galactitol compounds of this invention in the form of pharmaceutically acceptable salts. Such salts must clearly have a pharmaceutically acceptable anion or cation. Suitable pharmaceutically acceptable acid addition salts of the compounds of the present invention can be derived, when possible, from inorganic acids such as hydrochloric, hydrobromic, hydroiodic, phosphoric, metaphosphoric, nitric, sulfonic, and sulfuric acids, and organic acids such as acetic, adipic, alginic, aspartic, benzoic, benzenesulfonic, bisulfatic, butyric, camphoric, camphorsulfonic, citric, digluconic, cyclopentane-propionic, dodecylsulfatic, ethanesulfonic, gluconic, glycolic, glucoheptanoic, glycerophosphatic, hemisulfatic, heptanoic, hexanoic, fumaric, 2-hydroxy-ethanesulfonic, lactic, maleic, malic, methanesulfonic, nicotinic, 2-naphthalenesulfonic, oxalic, palmitic, pectinic, persulfatic, 3-phenylpropionic, picric, pivalic, propionic, succinic, tartaric, thiocyanic, toluenesulfonic, tosylic, mesylic, and undecanoic. The chloride salt is particularly preferred for medical purposes.

The present N-substituted-1,5-dideoxy-1,5-imino-D-glucitol or galactitol compounds have basic nitrogen atoms, and can be used in the form of a pharmaceutically acceptable salt thereof. The basic nitrogen-containing groups can be quaternized with agents such as lower alkyl halides, such as methyl, ethyl, propyl, and butyl chloride, bromides, and iodides; dialkyl sulfates such as dimethyl, diethyl, dibuytl, and diamyl sulfates; long chain halides such as decyl, lauryl, myristyl, and stearyl chlorides, bromides, and iodides; aralkyl halides such as benzyl and phenethyl bromides, and others. Water- or oil-soluble or dispersible products are thereby obtained as desired. The salts are formed by combining the basic compounds with the desired acid.

Other compounds of this invention that are acids can also form salts. Examples include salts with alkali metals or alkaline earth metals, such as sodium, potassium, calcium, or magnesium, or with organic bases or basic quaternary ammonium salts.

Compounds of this invention can be acids or bases. As such, they can be used to form salts with one another. This type of salt can then be provided to the patient in a pharmaceutically acceptable formulation or as a pure single salt.

Chemotherapeutic Agents

As indicated below, there are a large number of antineoplastic agents available in medical use, in clinical evaluation, and in pre-clinical development, that can be employed in the treatment of tumor cell growth in conjunction with the N-substituted-imino-D-glucitol or galactitol compounds of the present invention. Such antineoplastic agents fall into a number of major categories, including antibiotics (such as actinomycin D), antimetabolites, anthracyclines, alkaloids, alkylating agents, anti-microtubule agents (such as the vinca alkaloids and taxol), anti-tumor enzymes, hormonal agents, immunological agents, interferon-type agents, platinum-containing agents, topoisomerase inhibitors, DNA damaging agents (agents that cause breaks, such as single strand breaks, in DNA), and a category of miscellaneous agents. An example of a compound of this last category is carbetimer, which is an antineoplastic agent having significant cytotoxic activity in clonogenic assays (Kisner et al. (1983) Proc. ASCO 2) and in nude mice bearing a variety of human tumors (Ardalan et al. (1986) Cancer Res. 46).

Antineoplastic Compounds
17-Beta-Estradiol
Aclarubicin
Aldesleukin
Allopurinol
Altretamine
Amifostine
Amsacrine
Anastrozole
Asparaginase
Azidopine
BCG vaccine
BCNU
Bicalutamide
Bleomycin Sulfate
Busulfan
Carboplatin
Carmustine
Chlorambucil
Cisplatin
Cladribine
Clodronate disodium
Cyclophosphamide
Cytarabine
Cytarabine ocfosfate
Dacarbazine
Dactinomycin
Daunorubicin Hydrochloride
Dexrazoxane
Diethylstilbestrol
Docetaxel
Doxorubicin Hydrochloride Dronabinol
Eflornithine
Erythropoietin
Estramustine Phosphate Sodium
Etidronate Disodium
Etoposide
Etoposide phosphate
Fadrozole
Filgrastim
Fluasterone
Fludarabine Phosphate
Fluorouracil
Fluoxymesterone
Flutamide
Fluxuridine
Formestane
Fotemustine
Gallium Nitrate
Gemcitabine
Gemcitabine Hydrochloride
Goserelin Acetate
Granisetron Hydrochloride
Hexadecylphosphocholine
Hydroxyurea
Idarubicin
Idarubicin Hydrochloride
Ifosfamide
Interferon alfα-2a
Interferon alfα-2b
Interferon, Toray (beta)
Irinotecan
Irinotecan Hydrochloride
Lentinan
Letrozole
Leucovorin Calcium
Leuprolide Acetate
Levamisole
Lomustine
Lonidamine
Mechlorethamine Hydrochloride
Medroxyprogesterone Acetate
Megestrol Acetate
Melphalan
Mercaptopurine
Methotrexate Sodium
Mitolactol
Mitomycin
Mitotane
Mitoxantrone Hydrochloride
Nedaplatin
Nilutamide
Octreotide Acetate
Ondansetron Hydrochloride
Oxaliplatin
Paclitaxel
Pamidronate Disodium
Pegasparagase
Pegaspargase
Pentostatin
Pilocarpine
Pirarubicin
Plicamycin
Porfimer Sodium
Procarbazine Hydrochloride
Raltitrexed
Romurtide
Sargramostim
Sizofilan
Sobuzoxane
Streptozocin 2-deoxy-2-(((methylnitrosoamino) carbonyl) amino)-alpha(and beta)-D-glucopyranose
Tamoxifen Citrate
Tegafur+uracil
TheraCys BCG Live
Thioguanine
Thiotepa
Topotecan
Topotecan Hydrochloride
Toremifene
Tretinoin
Vinblastine Hydrochloride
Vincristine Sulfate
Vinorelbine
Vinorelbine Tartrate
Zinostatin stimalamer
Ambamustine
Phenalon
Ukrain
Broxuridine
EF-13
EF-27
Emitefur
Liarozole
Mitoguazone
Pentostatin
Virulizin
Vorozole
9-aminocamptothecin
AC Vaccine Technology
AD-32
AG-337
ALRT-1057
Adenocarcinoma vaccine
Anti-Her-2 MAb
AS-101
Autolymphocyte therapy
CGP-19835A
Cancer therapy, Aquila Biopharmaceuticals
Crisnatol mesylate
Dexaminoglutethimide
Diaziquone
Droloxifene
Exemestane
FGN-1
Fenretinide
GMK
ICI-182780
JM-216
LGD-1069
Lisofylline
M-Vax
Marimastat
Maxamine
Neovastat
Onconase
PALA
Peldesine
Piritrexim
Porfiromycin
Regressin
SDZ-PSC-833
SnET2
Suramin Temoporfin
Temozolomide
Tiazofurin
Tirapazamine
506U78
776C85
AGM-1470
ALRT-1550
Adenosine triphosphate
Alanosine
Aminopterin
Amrubicin
Annamycin
Anti-Bcl2 oligonucleotides
Antineoplaston A10
Antineoplaston AS2-1
BCH-4556
BEC-2
BMS-182248-01
BPA
Bisnafide
budotitane
CM-101
CTP-37
Calicheamicin
cancer vaccines, Wistar
Capecitabine
Carboxypeptidase
Carzelesin
cystemustine
DA-125
DRAC
DPPE
Decitabine
Didemnin B
Didox
EB-1089
EL-530
EL-532
E09
ET-743
GBC-590
GL-331
Gd-Tex
HN-66000
HP-228
Homoharringtonine
IST-622
Idoxifene
Ifosfamide+methylene blue
Interleukin-3 synthokine
KRN-5500
KRN-8602
L-Vax
LY-231514
Ledoxantrone trihydrochloride
Lobaplatin
Lometrexol
Lu-Tex
MAK therapy
MAK-BAb
MGDF
MS-209
Melanoma vaccine
Metesind glucuronate
Miproxifene phosphate
NK-611
NKS01
Nemorubicin
Nitrullyn
NOAC
O-Vax
OC-TR
ONO-4007
POLYDAN
PPI-149
RF110
RFS-2000
RII retinamide
RMP-7
Rhizoxin
S-1
SKI-2053R
Theradigm-melanoma
VX-710
VX-853
YM-511
42/6 Antibody
5-FP
AG-2034
AG-3340
Abiraterone acetate
BTG
Acemannan
Adenocarcinoma vaccine
Adenosine triphosphate
Alnorin
Antide
Aphidicolin glycinate
Asulacrine
BAB-447
BBR-2778
BCH-4556
BIWB-1
Bizelesin
Bryostatin-1
CEP-2563
CGP-41251
CGP-48664A
CGP-55847
CI-994
CT-2584
Cancer vaccine, Genzyme
Clomesone
Cordecypin
Crisnatol mesylate
Cyclocreatine
D-19575
D-21266
DX-8951f
Diethylnorspermine
Dolastatin-10
Edatrexate
EM-800
FCE-28068
FK-317
Flavopiridol
GF-120918
Intoplicine
KT-6149
KW-2170
KW-2189
LU-103793
LU-79553

LY-309887
Lymphoma vaccine, Apollon
MAC-DC
MDAM
ME-2906
Melanoma vaccine, UCLA
MEN-10755
MGI-114
MGV
MKC-454
Methioninase
Muc-1 vaccine
NB-506
Norcantharidin
OGT-719
OM-174
Oligonucleotide AML
OncoLipin-2
PG-2
PR-350
Peptide G
Pivaloyloxymethyl butyrate
Quinocarmycin monocitrate
S-16020-2
SDZ-62-434
SDZ-MKT-077
TAS-103
Theophylline
TherAmide
Theratope MUC-1
Titanocene dichloride
Tularemia live vaccine
Tumour vaccines, Medac
UCN-01
XR-5000
ZD-9331
ZnPc
A-007
C215FAb-SEA
CAI
Dilazep, chemoprotective
Gossypol
HSP cancer vaccine
Neuropeptides, ICRT
Perillyl alcohol
Paracelsian
TOP-53
TZT-1027

Methods for the preparation of many of the antineoplastic agents described above can be found in the literature. For example, methods for the preparation of doxorubicin are described in U.S. Pat. Nos. 3,590,028 and 4,012,448. Alternatively, certain agents are available commercially.

Pharmaceutical Compositions

The iminosugar and chemotherapeutic compounds employed in the methods of the present invention can be administered for their therapeutic purposes by any means that produce contact of these compounds with their site of action either in vitro or in vivo within the body. These compounds can be formulated separately, or together in a single pharmaceutical composition, along with a pharmaceutically acceptable carrier, diluent, or excipient. The carrier, etc., can be a solid, a liquid, or both, and is preferably formulated with the compound as a unit-dose composition, for example a tablet, which can contain from about 0.05% to about 95% by weight of the active compound(s). Other pharmacologically active substances can also be present.

The pharmaceutical compositions of the present invention can be prepared by any of the well known techniques of pharmacy, consisting essentially of appropriately admixing the components. The formulation of pharmaceuticals is discussed in, for example, *Remington's Pharmaceutical Sciences,* 16th Edition, Arthur Osol, Ed., Mack Publishing Co., Easton, Pa. (1980), and *Pharmaceutical Dosage Forms,* H. A. Liberman and L. Lachman, Eds., Marcel Decker, New York, N.Y. (1980).

The individual or combination pharmaceutical compositions of the present invention can be administered by any conventional means available for use in conjunction with pharmaceuticals. Pharmaceutical compositions according to the present invention include those suitable for oral, buccal (e.g., sublingual), parenteral (e.g., subcutaneous, intramuscular, intradermal, intrasternal, or intravenous injection, or infusion techniques), rectal, transdermal, and topical administration, as well as by inhalation spray, in dosage unit formulations containing conventional nontoxic pharmaceutically acceptable carriers, adjuvants, and vehicles as desired. Topical administration can involve the use of transdermal administration such as transdermal patches or iontophoresis devices.

For therapeutic purposes, formulations for parenteral administration, for example sterile injectable aqueous or oleaginous suspensions, can be formulated according to the known art in the form of aqueous or non-aqueous isotonic sterile injection solutions or suspensions using suitable dispersing or wetting agents and suspending agents. The sterile injectable preparation can also be a sterile injectable solution or suspension in a nontoxic, parenterally acceptable diluent or solvent, for example as a solution in 1,3-butanediol. These solutions and suspensions can be prepared from sterile powders or granules having one or more of the carriers or diluents mentioned for use in the formulations for oral administration. Pharmaceutically acceptable vehicles for the compounds of the present invention include water, polyethylene glycol, propylene glycol, ethanol, corn oil, cottonseed oil, peanut oil, Ringer's solution, sesame oil, benzyl alcohol, isotonic sodium chloride solution, and/or various buffers. In addition, sterile, fixed oils are conventionally employed as solvents or suspending media. For this purpose, any bland fixed oil can be employed, including synthetic mono-or diglycerides. In addition, fatty acids such as oleic acid are useful in the preparation of injectables. Other adjuvants and modes of administration are well and widely known in the pharmaceutical art. Injectable compositions according to the present invention can contain from about 0.1% to about 5% w/w of a compound disclosed herein.

Solid dosage forms for oral administration may include capsules, cachets, lozenges, tablets, or pills, each containing a predetermined amount of at least one compound of the present invention, or as powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water or other pharmaceutically acceptable non-aqueous liquid, or as an oil-in-water or water-in-oil emulsion. Such compositions can also comprise adjuvants, such as wetting agents, emulsifying and suspending agents, and sweetening, flavoring, and perfuming agents.

Pharmaceutical compositions suitable for buccal (sublingual) administration include lozenges comprising a compound of the present invention in a flavored base, usually sucrose, and acacia or tragacanth, and pastilles comprising the compound in an inert base such as gelatin and glycerin or sucrose and acacia.

Unit-dose suppositories for rectal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Pharmaceutical compositions suitable for topical application to the skin preferably take the form of an ointment, cream, lotion, paste, gel, spray, aerosol, or oil. Carriers that can be used include vaseline, lanolin, polyethylene glycols, alcohols, and combinations of two or more thereof. The active compound can be present at a concentration of from about 0.1% to about 15% w/w of the composition, for example, from about 0.5% to about 2%.

Transdermal administration is also possible. Pharmaceutical compositions suitable for transdermal administration can be presented as discrete patches adapted to remain in intimate contact with the epidermis of the recipient for a prolonged period of time. Such patches suitable contain a compound of the present invention in an optionally buffered, aqueous solution, dissolved and/or disperesed in an adhesive, or dispersed in a polymer. A suitable concentration of the active compound is in the range of from about 1% to about 35%, w/w, more preferably from about 3% to about 15%. As one particular possibility, the compound can be delivered from the patch by electrotransport or iontophoresis, for example, as described in *Pharmaceutical Research* (1986) 3:318.

Pharmaceutically acceptable carriers encompass all the foregoing and the like.

In addition to the foregoing types of pharmaceutical compositions, the iminosugars and chemotherapeutic compounds of the present invention can be administered in the form of delayed release or controlled release pharmaceutical preparations, i.e., pharmaceutical preparations designed to delay and/or extend the time over which the active drug molecule(s) is (are) delivered to the site of action by manipulation of the dosage form. In both cases, release of the pharmaceutically active agent is such that a pharmaceutically effective amount thereof capable of achieving its intended effect is present in vitro or in vivo over an extended period of time. Encompassed within the scope of the present invention, therefore, are such preparations, wherein either drug is present separately, both drugs are present together, or wherein both drugs are present together in a single formulation, but wherein one or the other of the iminosugar or chemotherapeutic compound is present in delayed or controlled release form, and the other is not. Delayed and/or controlled release of the present iminosugar compounds is preferred due to their pharmacokinetic properties, i.e., the desirability of maintaining a constant blood serum level thereof over a prolonged period.

This can be achieved by a number of different mechanisms, including, for example, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, enzymatic release of the active drug from the dosage form, etc. Delayed delivery dosage formulations are disclosed in U.S. Pat. No. 5,190,765. Slow release pharmaceutical compositions are also well known in the art. For example, U.S. Pat. No. 4,524,060 discloses a composition in the form of a non-compressed pellet having an enteric coat or a sustained release coat permeable to gastrointestinal juices. Other controlled release formulations are described in U.S. Pat. Nos. 4,880,830 and 5,068,112.

In addition to the delayed release and controlled release dosage formulations discussed above, there are dosage forms known in the art for delivering drugs continuously over time such as those disclosed in U.S. Pat. Nos. 4,327,725, 4,612,008, 4,765,989, and 4,783,337 that comprise a semipermeable wall surrounding a compartment. The compartment contains a drug formulation and a displacement member that pushes the drug formulation from the dosage form when fluid is imbibed by the dosage form through the semipermeable wall. Such dosage forms can deliver difficult to deliver drugs for their intended purpose. Another type of controlled release drug formulation or device is the gliadel wafer (Guilford Pharmaceutical). This vehicle can be used for local administration, for example in a tumor bed, for example that in a brain tumor, of a chemotherapeutic agent such as BCNU.

In any case, the amount of active ingredient that can be combined with the carrier materials to produce a single dosage form to be administered will vary depending upon the patient, the nature of the formulation, and the mode of administration.

Certain of the pharmaceutical compounds of this invention which are administered in accordance with the methods of the invention can serve as prodrugs to other compounds of this invention. Prodrugs are drugs that can be chemically converted in vivo or in vitro by biological systems into an active derivative or derivatives. Prodrugs are administered in essentially the same fashion as the other pharmaceutical compounds of the invention. Non-limiting examples are the esters of the N-substi-tuted-1,5-dideoxy-1,5-imino-D-glucitol or galactitol compounds of this invention.

It should be noted that the pharmaceutical compositions of the present invention can contain individual iminosugars, or combinations thereof, in anti-MDR effective doses. These iminosugars can also be used in combination with anti-MDR effective amounts of other compounds useful as anti-MDR agents, such as verapamil, tamoxifen, cyclosporin A, etc. In addition, the present invention encompasses pharmaceutical compositions comprising at least one of the present N-substituted-1,5-dideoxy-1,5-imino-D-glucitol or galactitol compounds and at least one anti-tumor chemotherapeutic compound. In such combined compositions, the iminosugar should be present in an anti-MDR effective amount, and the anti-tumor chemotherapeutic compound should be present in an anti-tumor effective amount. Specific dosages are discussed in detail below.

Administration

The N-substituted-1,5-dideoxy-1,5-imino-D-glucitol or galactitol compounds and one or more antineoplastic agents can be administered either sequentially in separate formulations, or simultaneously in a single formulation. Either the iminosugar or the antineoplastic agent, or both, can be used in combination with a liposome formulation to deliver the iminosugar and/or antineoplastic agent to the target tumor while protecting more sensitive tissue from the toxic effect of the antineoplastic agent. Administration can be effected by the route appropriate to the formulation of the pharmaceutical composition, discussed above. Administration by oral route is preferred in the case of the present iminosugars, but other routes are acceptable. Administration of anti-neoplastic chemotherapeutic agents can be by any conventional route therefor, which includes oral route, or intravenous, intra-muscular, or subcutaneous injection or infusion. Administration of phamaceutical compositions comprising both an iminosugar and an antineoplastic chemotherapeutic agent can thus be performed by any acceptable route compatible with both classes of compounds contained therein, such as the latter routes. Combination formulations can be in the form of a bolus, or in the form of aqueous or non-aqueous isotonic sterile injection solutions or suspensions. These solutions and suspensions can be prepared from sterile powders or granules having one or more pharmaceutically acceptable carriers, excipients, or diluents, or a binder such as gelatin or hydroxypropyl-methyl cellulose, together with one or more of a lubricant, preservative, surface-active agent, or dispersing agent.

Dosages

Imino Sugars

To prevent, reduce, or reverse MDR during chemotherapy, the N-substituted-1,5-dideoxy-1,5-imino-D-glucitol and/or galactitol compounds of the present invention should be administered to humans, or domestic animals such as cats and dogs, in an anti-MDR effective amount. Functionally, an effective amount is an amount, by whatever route administered, that results in a blood serum concentration in the range of from about 5 $\mu$M to about 500 $\mu$M, preferably from about 10 $\mu$M to about 250 $\mu$M, more preferably from about 15 $\mu$M to about 100 $\mu$M, and even more preferably from about 20 $\mu$M to about 60 $\mu$M. About 50 $\mu$M is a preferred concentration. This can be achieved by administration of these compounds in an amount in the range of from about 10 mg/day to about 3,000 mg/day, more preferably from about 100 mg/day to about 3,000 mg/day, and most preferably from about 1,000 mg/day to about 3,000 mg/day. About 3,000 mg/day is a preferred dose. When administered in non-sustained release formulations, the total daily dose of iminosugars indicated above can be administered in equal, one-third subdoses administered at eight hour intervals, e.g., about 1,000 mg every eight hours. When a sustained-release preparation is employed, the total daily dose can be administered at one time. In either case, the pharmaceutical composition should contain an amount of iminosugar effective to achieve a blood serum level in the micromolar ranges indicated above over successive 8 hour intervals.

In a 24 week study of the safety and efficacy of N-butyl DNJ and zidovudine in patients with HIV-1 infection, Fischl et al. ((1994) *J. Acquired Immune Defic. Syndr.* 7:139) noted that the major toxicity associated with administration of 3,000 mg/day of N-butyl DNJ was diarrhea. These authors suggested that such diarrhea could be alleviated with a low complex carbohydrate diet and/or antidiarrheal medications.

N-alkylated glucitol and galactitol iminosugars each possess distinct advantages in the methods of the present invention. N-butyl DNJ does not inhibit the galactosyltransferase that initiates the biosynthesis of galactosylceramide (GalCer)-based glycosphingolipids (GalCer and sulfatide), which are important constituents of myelin. Thus, N-butyl DNJ and related glucitol derivatives will not impair myelination and myelin stability in patients in which this is a concern.

On the other hand, in patients in which inhibition of $\alpha$-glucosidase I and II or lysosomal $\beta$-glucocerebrosidase is undesirable, N-alkyl galactitol iminosugars may be preferred in view of the specificity of compounds such as N-butyl DGJ in inhibiting glycosphingolipid biosynthesis (Platt et al. (1994) *J. Biol. Chem.* 269:27108–27114).

In some situations, it may be desirable to use a pharmaceutical composition comprising a combination of an N-alkyl glucitol and an N-alkyl galactitol iminosugar to avoid or ameliorate the effects of MDR during chemotherapy. Together, such iminosugars should comprise an anti-MDR effective amount.

Chemotherapeutic Agents

Guidelines for drug selection and dosage for the treatment of cancer can be found in *Cancer: Principles & Practice of Oncology*, 6th Edition, 1996, Vincent T. DeVita, Jr. et al., Eds., J. B. Lippincott Company, Philadelphia.

Due to suppression of MDR via the use of the N-substituted-1,5-dideoxy-1,5-imino-D-glucitol or galactitol compounds of the present invention, the medical practitioner will be able to administer conventional amounts of chemotherapeutic agents, or perhaps even reduced amounts thereof, by employing the methods and compositions disclosed herein. Such reduced amounts can be determined in patients undergoing chemotherapy by routine monitoring of tumor antigens, such as the CEA, PSA, or CA15-3 antigens, in patient serum, or in body tissues by other immunological methods; X-ray studies; radiographic imaging of tumors; CT, MRI, ultrasound, or PET scanning; biopsy; palpation; observation of the general state of the patient, performance status, etc., as is well known in the art. Thus, patients can be monitored during chemotherapy in conjunction with the administration of N-substituted- 1,5-dideoxy-1,5-imino-D-glucitol and/or galactitol compounds and antineoplastic agents to determine the lowest effective doses of each.

The doses described above can be administered to a patient in a single dose or in proportionate multiple subdoses. In the latter case, dosage unit compositions can contain such amounts of submultiples thereof to make up the total dose. Multiple subdoses can also be administered to increase the total dose should this be desired by the person prescribing the drug.

Combination Pharmaceutical Compositions

As noted above under "Pharmaceutical Compositions," the iminosugar and chemotherapeutic compounds employed in the methods of the present invention can be formulated in single pharmaceutical compositions comprising both classes of drugs. Such compositions should contain an iminosugar in an anti-MDR effective dosage amount and an anti-tumor chemotherapeutic compound in an anti-tumor effective dosage amount. An anti-MDR effective dosage amount of an iminosugar is an amount, by whatever route administered, that results in a blood serum concentration in the range of from about 5 $\mu$M to about 500 $\mu$M, preferably from about 10 $\mu$M to about 250 $\mu$M, more preferably from about 15 $\mu$M to about 100 $\mu$M, and even more preferably from about 20 $\mu$M to about 60 $\mu$M. About 50 $\mu$M is a preferred concentration. When administered in a delayed or controlled release formulation, this can be achieved by administration of these compounds in an amount in the range of from about 10 mg/day to about 3,000 mg/day, more preferably from about 100 mg/day to about 3,000 mg/day, and most preferably from about 1,000 mg/day to about 3,000 mg/day. About 3,000 mg/day is a preferred dose. Non-controlled release formulations should contain one-third of the total daily dose, e.g., about 1,000 mg, and should be administered to the patient at eight hour intervals.

Dosages for antineoplastic agents are described in *Cancer: Principles & Practice of Oncology*, 6th Edition, 1996, Vincent T. DeVita, Jr. et al., Eds., J. B. Lippincott Company, Philadelphia, or are otherwise known in the art. When administered in a delayed or controlled release form combination formulation containing an iminosugar, both the antineoplastic agent and the iminosugar can be administered in their standard daily, single administration dose. When administered in a combination formulation containing an iminosugar in non-controlled release form, the antineoplastic agent can be present in an amount totalling one-third of the total daily dose; such non-sustained release combination formulations should be administered to the patient at eight hour intervals to achieve the desired, total daily doses of both drugs. Alternatively, when an appropriate antineoplastic agent is given, the total daily dose of such antineoplastic agent can be present in controlled or non-controlled release form for once daily administration, and the iminosugar can be present in non-controlled release form equivalent to one-third of the total daily dose, the two remaining one-third daily subdoses of the iminosugar being administered at subsequent eight hour intervals during the remainder of the day.

Treatment Regimen

The regimen for treating a patient undergoing chemotherapy with the compounds and/or compositions of the present invention is selected in accordance with a variety of factors, including the age, weight, sex, diet, and medical condition of the patient, the severity of the cancer, the route of administration, pharmacological considerations such as the activity, efficacy, pharmacokinetic, and toxicology profiles of the particular compounds employed, and whether a drug delivery system is utilized.

Typical chemotherapeutic regimens comprise a course of six to eight cycles of treatment, each cycle typically involving administration of antineoplastic drugs over the course of three to four weeks.

The N-substituted-1,5-dideoxy-1,5-imino-D-glucitol or galactitol compounds of the present invention can be administered daily to patients receiving chemotherapy in accordance with a number of different regimens. Fundamentally, these iminosugars should be administered in an anti-MDR effective amount for a period of time effective to exert their MDR preventing, reducing, or reversing action on tumor cells. Without wishing to be bound by any particular theory of this invention, the inventor hypothesizes that this effect may be achieved by inhibition of UDP-glucose-N-acyl-sphingosine glucosyltransferase (EC 2.4.1.80) for a period of time sufficient to decrease the levels of glucosylceramide, and subsequently, more complex glycosphingolipids and gangliosides, in the membranes of cancerous cells. Based upon results obtained in in vitro systems and Tay-Sachs mice, administration can commence in a period in the range of from about 14 days to about three days prior to administration of the chemotherapeutic agent(s), and can continue daily thereafter, up to and including administration of the chemotherapeutic agent. Administration of these iminosugars can be continued daily for a brief period, e.g., about one to about five days after administration of the chemotherapeutic agent, to alleviate or avoid potential MDR effects during the period in which residual amounts of chemotherapeutic agents remain in tumor cells.

Therefore, in general, the N-substituted-1,5-dideoxy-1,5-imino-D-glucitol or galactitol compounds of the present invention can be administered prior to administration of the chemotherapeutic agent. The N-substituted-1,5-dideoxy-1,5-imino-D-glucitol or galactitol compounds can also be administered both prior to and simultaneously with administration of the chemotherapeutic agent; or simultaneously with administration of the chemotherapeutic agent; or prior to, simultaneously with, and subsequently to administration of the chemotherapeutic agent; or prior to and subsequently to administration of the chemothera-peutic agent.

More particularly, the present N-substituted-1,5-dideoxy-1,5-imino-D-glucitol or galactitol compounds can be administered daily to the patient in a time period starting from about 14 days prior to administration of the chemotherapeutic agent. More preferably, these iminosugars can be administered daily to the patient in a time period starting from about 10 days prior to administration of the chemotherapeutic agent. In some patients, it may be necessary or desirable to commence administration of these iminosugars about 7 days prior to administration of the chemotherapeutic agent. In other cases, administration of these iminosugars can commence about 5 days, or even about 3 days, prior to administration of the chemotherapeutic agent. As indicated above, these iminosugars can be further administered simultaneously with the chemotherapeutic agent, and/or subsequently to administration of the chemotherapeutic agent, on a daily basis for a period in the range of from about one to about five days, preferably for about two days, after administration of each dose of the chemotherapeutic agent.

Administration of the N-substituted-1,5-dideoxy-1,5-imino-D-glucitol or galactitol compounds of the present invention should be continued in conjunction with the prescribed chemotherapeutic regimen as outlined above until the cancer has been controlled or eradicated.

The proven long-term safety associated with the administration of the iminosugars disclosed herein (note, for example, Fischl et al. ((1994) *J. Acquired Immune Defic. Syndr.* 7:139, in this regard) also permits another regimen: the present N-alkylated glucitol and galactitol derivatives can be administered on a daily basis throughout the entire course of the patient's chemotherapy. Rather than administering these compounds only in anticipation of individual chemotherapy sessions as described above, the practitioner can order continuous daily administration thereof. In this regimen, and in a manner similar to that of the regimens described above, administration of the present N-alkylated glucitol and galactitol derivatives can commence about 14 days, about 10 days, about 7 days, about 5 days, or about 3 days prior to administration of the initial dose of the chemotherapeutic drug, and continue on a daily basis thereafter.

As previously noted, patients undergoing treatment with the drug combinations disclosed herein can be routinely monitored by measuring serum antigen levels, by radiographic imaging of tumors, biopsy, palpation, etc., to determine the effectiveness of therapy.

Continuous analysis of the data obtained by the foregoing methods permits modification of the treatment regimen during chemotherapy so that optimal amounts of the N-alkyl-1,5-dideoxy-1,5-imino-D-glucitol and galactitol compounds of this invention and chemotherapeutic agent(s) are administered, and so that the duration of treatment can be determined as well. Thus, the treatment regimen/dosing schedule can be rationally modified over the course of chemotherapy so as to achieve the lowest doses of each of the N-substituted-1,5-dideoxy-1,5-imino-D-glucitol or galactitol compounds of this invention and the chemotherapeutic agent(s), which together result in satisfactory anti-cancer effectiveness, and so that administration of these compounds is continued only so long as is necessary to successfully treat the cancer.

The following non-limiting examples serve to illustrate various aspects of the present invention.

EXAMPLE 1

Preparation of 1,5-(butylimino)-1,5-dideoxy-D-glucitol

A solution of 1,5-dideoxy-1,5-imino-D-glucitol (5.14 g, 0.0315 mole), butyraldehyde (3.35 ml, 0.0380 mole) and Pd black (1 g) in 200 ml methanol is hydrogenated (60 psi/29° C./21 hrs.). After filtering the resulting mixture, the filtrate is concentrated in vacuo to an oil. The title compound is crystallized from acetone, and recrystallized from methanol/acetone, m.p. ca. 132° C. The structure assignment is supported by NMR, infrared spectra and elemental analysis.

Analysis calcd. for $C_{10}H_{21}NO_4$: C, 54.78; H, 9.65; N, 6.39. Found: C, 54.46; H, 9.33; N, 6.46.

EXAMPLE 2

Preparation of 1,5-(butylimino)-1,5-dideoxy-D-glucitol, tetraacetate

Acetic anhydride (1.08 g, 0.0106 mole) is added to the title compound of Example 1 (0.50 g, 0.0023 mole) in 5 ml pyridine and stirred for 17 days at room temperature. The product is evaporated under nitrogen gas. The resulting title compound is purified by silica gel chromatography. The structure assignment is supported by NMR, infrared spectra, and elemental analysis.

Analysis calcd. for $C_{18}H_{29}O_8$: C, 55.80; H, 7.54; N, 3.62. Found: C, 55.42; H, 7.50; N, 3.72.

EXAMPLE 3

Preparation of 1,5-(butylimino)-1,5-dideoxy-D-galactitol 30 mg (184 μmol) of deoxygalactonojirimycin are dissolved in 1 ml of 50 mM sodium acetate buffer, pH 5.0, to which 20 mg of palladium black is added. A hydrogen atmosphere is maintained in the reaction vessel, and 100 μl (1.1 mmol) of butyraldehyde are introduced. The reaction is stirred for 16 hr. at room temperature (ca. 20° C.). The reaction is stopped by filtration through a bed (1 g) of Celite (30–80 mesh), and the reaction products are separated by chromatography using a column containing 4 ml of packed Dowex® AG5O-X12 (H+ form) resin. The N-butyl DGJ is eluted from the column with 2M ammonia, and its molecular mass and chemical structure determined by laser desorption mass spectrometry and 1D $^1$H NMR, respectively.

EXAMPLE 4

Preparation of 1,5-(propylimino)-1,5-dideoxy-D-galactitol

The synthetic procedure and compound analysis of Example 3 can be repeated, except that propanoyl aldehyde can be substituted for an equivalent amount of butyraldehyde for analogous preparation of N-propyl DGJ.

EXAMPLE 5

Preparation of 1,5-(hexylimino)-1,5-dideoxy-D-galactitol

The synthetic procedure and compound analysis of Example 3 can be repeated, except that caproaldehyde can be substituted for an equivalent amount of butyraldehyde for analogous preparation of N-hexyl DGJ.

N-alkyl DGJ compounds prepared as described in foregoing Examples 3–5 can be obtained in overall yields of 68–74% based on the starting DGJ, and in greater than 95% purity.

The invention being thus described, it will be obvious that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A method for preventing, reducing, or reversing multidrug resistance in a patient undergoing treatment with a chemotherapeutic agent, comprising administering to said patient an anti-multidrug resistance effective amount of an N-substituted-1,5-dideoxy-1,5-imino-D-glucitol or galactitol compound of Formula I:

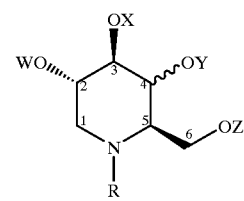

wherein R is selected from the group consisting of arylalkyl, cycloalkylalkyl, and branched or straight chain alkyl having a chain length of $C_2$ to $C_{20}$, and W, X, Y and Z are independently selected from the group consisting of hydrogen, alkanoyl, aroyl, and trifluoroalkanoyl, or a pharmaceutically acceptable salt thereof, for a period of time effective to prevent, reduce, or reverse multidrug resistance in cancer cells of said patient.

2. The method of claim 1, wherein said N-substituted-1,5-dideoxy-1,5-imino-D-glucitol or galactitol compound is administered prior to administration of said chemotherapeutic agent.

3. The method of claim 1, wherein said N-substituted-1,5-dideoxy-1,5-imino-D-glucitol or galactitol compound is administered both prior to and simultaneously with administration of said chemotherapeutic agent.

4. The method of claim 1, wherein said N-substituted-1,5-dideoxy-1,5-imino-D-glucitol or galactitol compound is administered prior to, simultaneously with, and subsequently to administration of said chemotherapeutic agent.

5. The method of claim 1, wherein said N-substituted-1,5-dideoxy-1,5-imino-D-glucitol or galactitol compound is administered prior to and subsequently to administration of said chemotherapeutic agent.

6. The method of claim 1, wherein said N-substituted-1,5-dideoxy-1,5-imino-D-glucitol or galactitol compound is administered daily throughout the course of treatment with said chemotherapeutic agent.

7. The method of claim 1, wherein said N-substituted-1,5-dideoxy-1,5-imino-D-glucitol or galactitol compound is administered daily to said patient commencing in a period from about 14 days to about three days prior to administration of said chemotherapeutic agent.

8. The method of claim 7, further comprising administering an effective amount of said N-substituted-1,5-dideoxy- 1,5-imino-D-glucitol or galactitol compound for a period of time effective to alleviate multidrug resistance effects subsequent to administration of said chemotherapeutic agent.

9. The method of claim 8, wherein said period of time effective to alleviate multidrug resistance effects subsequent to administration of said chemotherapeutic agent is in the range of from about one to about five days after administration of said chemotherapeutic agent.

10. The method of claim 1, wherein said effective amount of said N-substituted-1,5-dideoxy-1,5-imino-D-glucitol or galactitol compound is administered in a one-third divided subdose every eight hours.

11. The method of claim 1, wherein R is a straight or branched chain alkyl group having a chain length of $C_2$ to $C_{20}$, and W, X, Y, and Z are each hydrogen.

12. The method of claim 11, wherein R is a straight chain alkyl group having a chain length of $C_4$ to $C_{20}$.

13. The method of claim 12, wherein R is a straight chain alkyl group having a chain length of $C_4$ to $C_{14}$.

14. The method of claim 13, wherein R is a straight chain alkyl group having a chain length of $C_4$ to $C_{10}$.

15. The method of claim 14, wherein R is a straight chain alkyl group having a chain length of $C_4$ to $C_8$.

16. The method of claim 15, wherein R is a straight chain alkyl group having a chain length of $C_4$ to $C_6$.

17. The method of claim 16, wherein R is n-butyl.

18. The method of claim 16, wherein R is n-hexyl.

19. The method of claim 1, wherein R is a straight or branched chain alkyl group having a chain length of $C_2$ to $C_{20}$, and W, X, Y, and Z are each an alkanoyl group having a chain length of $C_1$ to $C_{20}$.

20. The method of claim 19, wherein R is a straight chain alkyl group having a chain length of $C_4$ to $C_{20}$.

21. The method of claim 1, wherein said N-substituted-1,5-dideoxy-1,5-imino-D-glucitol or galactitol compound is selected from the group consisting of:

N-(n-ethyl-)-1,5-dideoxy-1,5-imino-D-glucitol or galactitol;
N-(n-propyl-)-1,5-dideoxy-1,5-imino-D-glucitol or galactitol;
N-(n-butyl-)-1,5-dideoxy-1,5-imino-D-glucitol or galactitol;
N-(n-hexyl-)-1,5-dideoxy-1,5-imino-D-glucitol or galactitol;
N-(n-heptyl-)-1,5-dideoxy-1,5-imino-D-glucitol or galactitol;
N-(n-octyl-)-1,5-dideoxy-1,5-imino-D-glucitol or galactitol;
N-(n-octyl-)-1,5-dideoxy-1,5-imino-D-glucitol or galactitol, tetrabutyrate;
N-(n-nonyl-)-1,5-dideoxy-1,5-imino-D-glucitol or galactitol, tetrabutyrate;
N-(n-decyl-)-1,5-dideoxy-1,5-imino-D-glucitol or galactitol, tetrabutyrate;
N-(n-undecyl-)-1,5-dideoxy-1,5-imino-D-glucitol or galactitol, tetrabutyrate;
N-(n-nonyl-)-1,5-dideoxy-1,5-imino-D-glucitol or galactitol;
N-(n-decyl-)-1,5-dideoxy-1,5-imino-D-glucitol or galactitol;
N-(n-undecyl-)-1,5-dideoxy-1,5-imino-D-glucitol or galactitol;
N-(n-dodecyl-)-1,5-dideoxy-1,5-imino-D-glucitol or galactitol;
N-(2-ethylhexyl)-1,5-dideoxy-1,5-imino-D-glucitol or galactitol;
N-(4-ethylhexyl)-1,5-dideoxy-1,5-imino-D-glucitol or galactitol;
N-(5-methylhexyl)-1,5-dideoxy-1,5-imino-D-glucitol or galactitol;
N-(3-propylhexyl)-1,5-dideoxy-1,5-imino-D-glucitol or galactitol;
N-(1-pentylpentylhexyl)-1,5-dideoxy-1,5-imino-D-glucitol or galactitol;
N-(1-butylbutyl)-1,5-dideoxy-1,5-imino-D-glucitol or galactitol;
N-(7-methyloctyl-)-1,5-dideoxy-1,5-imino-D-glucitol or galactitol;
N-(8-methylnonyl)-1,5-dideoxy-1,5-imino-D-glucitol or galactitol;
N-(9-methyldecyl)-1,5-dideoxy-1,5-imino-D-glucitol or galactitol;
N-(10-methylundecyl)-1,5-dideoxy-1,5-imino-D-glucitol or galactitol;
N-(6-cyclohexylhexyl-)-1,5-dideoxy-1,5-imino-D-glucitol or galactitol;
N-(4-cyclohexylbutyl)-1,5-dideoxy-1,5-imino-D-glucitol or galactitol;
N-(2-cyclohexylethyl)-1,5-dideoxy-1,5-imino-D-glucitol or galactitol;
N-(1-cyclohexylmethyl)-1,5-dideoxy-1,5-imino-D-glucitol or galactitol;
N-(1-phenylmethyl)-1,5-dideoxy-1,5-imino-D-glucitol or galactitol;
N-(3-phenylpropyl)-1,5-dideoxy-1,5-imino-D-glucitol or galactitol;
N-(3- (4-methyl)-phenylpropyl)-1,5-dideoxy-1,5-imino-D-glucitol or galactitol;
N-(6-phenylhexyl)-1,5-dideoxy-1,5-imino-D-glucitol or galactitol;
N-(n-nonyl-)-1,5-dideoxy-1,5-imino-D-glucitol or galactitol, tetrabutyrate;
N-(n-decyl-)-1,5-dideoxy-1,5-imino-D-glucitol or galactitol, tetrabutyrate;
N-(n-undecyl-)-1,5-dideoxy-1,5-imino-D-glucitol or galactitol, tetrabutyrate;
N-(n-dodecyl-)-1,5-dideoxy-1,5-imino-D-glucitol or galactitol, tetrabutyrate;
N-(2-ethylhexyl)-1,5-dideoxy-1,5-imino-D-glucitol or galactitol, tetrabutyrate;
N-(4-ethylhexyl)-1,5-dideoxy-1,5-imino-D-glucitol or galactitol, tetrabutyrate;
N-(5-methylhexyl)-1,5-dideoxy-1,5-imino-D-glucitol or galactitol, tetrabutyrate;
N-(3-propylhexyl)-1,5-dideoxy-1,5-imino-D-glucitol or galactitol, tetrabutyrate;
N-(1-pentylpentylhexyl)-1,5-dideoxy-1,5-imino-D-glucitol or galactitol, tetrabutyrate;
N-(1-butylbutyl)-1,5-dideoxy-1,5-imino-D-glucitol or galactitol, tetrabutyrate;
N-(7-methyloctyl-)-1,5-dideoxy-1,5-imino-D-glucitol or galactitol, tetrabutyrate;
N-(8-methylnonyl)-1,S-dideoxy-1,5-imino-D-glucitol or galactitol, tetrabutyrate;
N-(9-methyldecyl)-1,5-dideoxy-1,5-imino-D-glucitol or galactitol, tetrabutyrate;
N-(10-methylundecyl)-1,5-dideoxy-1,5-imino-D-glucitol or galactitol, tetrabutyrate;
N-(6-cyclohexylhexyl-)-1,5-dideoxy-1,5-imino-D-glucitol or galactitol, tetrabutyrate;
N-(4-cyclohexylbutyl)-1,5-dideoxy-1,5-imino-D-glucitol or galactitol, tetrabutyrate;
N-(2-cyclohexylethyl)-1,5-dideoxy-1,5-imino-D-glucitol or galactitol, tetrabutyrate;
N-(1-cyclohexylmethyl)-1,5-dideoxy-1,5-imino-D-glucitol or galactitol, tetrabutyrate;
N-(1-phenylmethyl)-1,5-dideoxy-1,5-imino-D-glucitol or galactitol, tetrabutyrate;

N-(3-phenylpropyl)-1,5-dideoxy-1,5-imino-D-glucitol or galactitol, tetrabutyrate;

N-(3-(4-methyl)-phenylpropyl)-1,5-dideoxy-1,5-imino-D-glucitol or galactitol, tetrabutyrate; and N-(6-phenylhexyl)-1,5-dideoxy-1,5-imino-D-glucitol or galactitol, tetrabutyrate, or a pharmaceutically acceptable salt thereof.

22. The method of claim 21, wherein said N-substituted-1,5-dideoxy-1,5-imino-D-glucitol or galactitol compound is selected from the group consisting of N-(n-butyl)-1,5-dideoxy-1,5-imino-D-glucitol or galactitol and N-(n-hexyl)-1,5-dideoxy-1,5-imino-D-glucitol or galactitol.

23. The method of claim 1, wherein said chemotherapeutic agent is selected from the group consisting of an alkaloid, a topoisomerase II inhibitor, and a DNA damaging agent.

24. The method of claim 23, wherein said alkaloid is a vinca alkaloid.

25. The method of claim 24, wherein said vinca alkaloid is selected from the group consisting of vincristine, vinblastine, and vindesine.

26. The method of claim 23, wherein said topoisomerase II inhibitor is selected from the group consisting of an anthracycline and an epipodophyllotoxin.

27. The method of claim 26, wherein said anthracycline is selected from the group consisting of doxorubicin, daunorubicin, idarubicin, and mitoxantrone.

28. The method of claim 26, wherein said epipodophyllotoxin is selected from the group consisting of etoposide and tenoposide.

29. The method of claim 23, wherein said DNA damaging agent is actinomycin D.

30. The method of claim 1, wherein said effective amount of said N-substituted-1,5-dideoxy-1,5-imino-D-glucitol or galactitol compound is an amount that results in a blood serum concentration in the range of from about 5 $\mu$M to about 500 $\mu$M by whatever route it is administered.

31. The method of claim 30, wherein said effective amount of said N-substituted-1,5-dideoxy-1,5-imino-D-glucitol or galactitol compound is an amount that results in a blood serum concentration in the range of from about 20 $\mu$M to about 60 $\mu$M by whatever route it is administered.

32. The method of claim 31, wherein said effective amount of said N-substituted-1,5-dideoxy-1,5-imino-D-glucitol or galactitol compound is an amount that results in a blood serum concentration of about 50 $\mu$M by whatever route it is administered.

33. The method of claim 1, wherein said effective amount of said N-substituted-1,5-dideoxy-1,5-imino-D-glucitol or galactitol compound is in the range of from about 10 mg/day to about 3,000 mg/day.

34. The method of claim 33, wherein said effective amount of said N-substituted-1,5-dideoxy-1,5-imino-D-glucitol or galactitol compound is in the range of from about 100 mg/day to about 3,000 mg/day.

35. The method of claim 34, wherein said effective amount of said N-substituted-1,5-dideoxy-1,5-imino-D-glucitol or galactitol compound is in the range of from about 1,000 mg/day to about 3,000 mg/day.

36. The method of claim 1, wherein said N-substituted-1,5-dideoxy-1,5-imino-D-glucitol or galactitol compound is administered orally or parenterally.

37. The method of claim 36, wherein said chemotherapeutic agent is administered parenterally.

38. The method of claim 37, wherein said parenteral administration is by slow intravenous infusion.

39. A method for preventing, reducing, or reversing multidrug resistance in a patient undergoing treatment with a chemotherapeutic agent selected from the group consisting of an alkaloid, a topoisomerase II inhibitor, an anti-microtubule agent, and a DNA damaging agent, comprising:

administering to said patient about 1,000 mg/day to about 3,000 mg/day of N-(n-butyl)-1,5-dideoxy-1,5-imino-D-glucitol or galactitol or N-(n-hexyl)-1,5-dideoxy-1,5-imino-D-glucitol or galactitol, or a pharmaceutically acceptable salt thereof, in three equal subdoses, each of which is administered at eight hour intervals, commencing about 10 days prior to administration of said chemotherapeutic agent, and continuing daily thereafter throughout the course of administration of said chemotherapeutic agent.

40. A pharmaceutical composition, comprising an anti-multidrug resistance effective amount of at least one N-substituted-1,5-dideoxy-1,5-imino-D-glucitol or galactitol compound of claim 1;

an anti-tumor effective amount of at least one anti-tumor chemotherapeutic compound; and a pharmaceutically acceptable carrier.

41. The pharmaceutical composition of claim 40, wherein both said N-substituted-1,5-dideoxy-1,5-imino-D-glucitol or galactitol compound and said anti-tumor chemotherapeutic compound are in controlled release form.

42. The pharmaceutical composition of claim 40, wherein only said N-substituted-1,5-dideoxy-1,5-imino-D-glucitol or galactitol compound is in controlled release form.

* * * * *